US006454705B1

(12) United States Patent
Cosentino et al.

(10) Patent No.: US 6,454,705 B1
(45) Date of Patent: Sep. 24, 2002

(54) MEDICAL WELLNESS PARAMETERS MANAGEMENT SYSTEM, APPARATUS AND METHOD

(75) Inventors: Louis C. Cosentino, Excelsior; Michael John Duea, Savage; Duane Robert Duea, Apple Valley; Steven George Dorfe, Maple Grove; Daniel L. Cosentino, Minnetonka, all of MN (US)

(73) Assignee: Cardiocom, Excelsior, MN (US)

( * ) Notice: Subject to any disclaimer, the term of this patent is extended or adjusted under 35 U.S.C. 154(b) by 0 days.

(21) Appl. No.: 09/399,041

(22) Filed: Sep. 21, 1999

(51) Int. Cl.$^7$ ................................................. A61B 5/00
(52) U.S. Cl. ....................... 600/300; 128/903; 128/904; 128/920; 600/301; 600/587; 600/592; 705/3
(58) Field of Search ................................ 600/300–301, 600/481–500, 529–546; 128/903–905, 920–925; 705/2–3

(56) References Cited

U.S. PATENT DOCUMENTS

| 3,925,762 A | 12/1975 | Heitlinger et al. |
| 4,531,527 A | 7/1985 | Reinhold, Jr. et al. |
| RE32,361 E | 2/1987 | Duggan |

(List continued on next page.)

FOREIGN PATENT DOCUMENTS

| DE | 43 35 869 A1 | 10/1994 |
| JP | 9173304 A | 7/1997 |
| WO | WO 98/40835 | 9/1998 |

OTHER PUBLICATIONS

Patel, U. et al., "A Computer–Based, Automated Telephonic System to Monitor Patient Progress in the Home Setting", *Journal of Medical Systems*, vol. 16, Nos. 2/3, pp. 101–112 (1992).

Yazolino, L., (title not legible), *Medical Electronics*, 4 pages (Sep. 1998).

"Telemedicine, Your Partner in Telemedicine", Aerotel Medical Systems, Ltd., Internet at http://www.aerotel.com/telemed/under.html, last updated Sep. 5, 1998.

"Technology to Help Meet Standards and Reduce Costs", Alere Medical Incorporated, 6 pages (1998).

*Primary Examiner*—Kevin Shaver
*Assistant Examiner*—Michael C Astorino
(74) *Attorney, Agent, or Firm*—Merchant & Gould P.C.

(57) ABSTRACT

A medical system, apparatus and method for monitoring and managing one or more ambulatory patients on a computer and allowing a caregiver to review the ambulatory patients' wellness parameters to provide treatment in accordance with the wellness parameters. The system, apparatus and method provides a patient monitoring apparatus having a first communication device associated therewith for monitoring a patient's wellness parameters. A central computer located remote from the monitoring apparatus and in communication therewith, the central computer having a second communication device associated therewith for communicating wellness parameters and treatment data over a communications link established between the central computer and the monitoring apparatus, the central computer being operated for querying the patient via the patient monitoring apparatus, receiving and processing measured wellness parameters from the monitoring apparatus and calculating a score according to the wellness parameters. A main database coupled to the central computer having patient medical records stored therein. One or more computer workstations located remote from the central computer and in communication therewith, the one or more computers having a third communication device associated therewith for communicating physical examination data between the central computer and the one or more workstations over a communication link established therebetween. The score calculated by the central computer according to the wellness parameters is compared with a predetermined value, and based on the results of the comparison the central computer issuing an exception report and communicating the exception report to the one or more workstations located remote therefrom, whereby a caregiver located at the remote workstation site is notified of the exception report.

26 Claims, 22 Drawing Sheets

U.S. PATENT DOCUMENTS

| | | |
|---|---|---|
| 4,712,562 A | 12/1987 | Ohayon et al. |
| 4,838,275 A | 6/1989 | Lee |
| 4,899,758 A | 2/1990 | Finkelstein et al. |
| 4,947,858 A | 8/1990 | Smith |
| 5,012,411 A | 4/1991 | Policastro et al. |
| 5,054,493 A | 10/1991 | Cohn et al. |
| 5,092,330 A | 3/1992 | Duggan |
| 5,241,966 A | 9/1993 | Finkelstein et al. |
| 5,307,263 A | 4/1994 | Brown |
| 5,331,549 A | 7/1994 | Crawford, Jr. |
| 5,390,238 A | 2/1995 | Kirk et al. |
| 5,402,794 A | 4/1995 | Wahlstrand et al. |
| 5,406,955 A | 4/1995 | Bledsoe et al. |
| 5,434,611 A | 7/1995 | Tamura |
| 5,437,285 A | 8/1995 | Verrier et al. |
| 5,441,047 A | 8/1995 | David et al. |
| 5,553,609 A | 9/1996 | Chen et al. |
| 5,553,623 A | 9/1996 | Ochs |
| 5,560,370 A | 10/1996 | Verrier et al. |
| 5,594,638 A | 1/1997 | Iliff |
| 5,660,176 A | 8/1997 | Iliff |
| 5,687,717 A | 11/1997 | Halpern et al. |
| 5,704,366 A | 1/1998 | Tacklind et al. |
| 5,711,297 A | 1/1998 | Iliff |
| 5,724,032 A | 3/1998 | Klein et al. |
| 5,724,968 A | 3/1998 | Iliff |
| 5,725,559 A | 3/1998 | Alt et al. |
| 5,743,267 A | 4/1998 | Nikolic et al. |
| 5,758,652 A | 6/1998 | Nikolic |
| 5,778,882 A | 7/1998 | Raymond et al. |
| 5,822,715 A | 10/1998 | Worthington et al. |
| 5,828,943 A | 10/1998 | Brown |
| 5,832,448 A | 11/1998 | Brown |
| 5,839,438 A | 11/1998 | Graettinger et al. |
| 5,842,997 A | 12/1998 | Verrier et al. |
| 5,843,139 A | 12/1998 | Goedeke et al. |
| 5,846,223 A | 12/1998 | Swartz et al. |
| 5,868,669 A | 2/1999 | Iliff |
| 5,879,163 A | 3/1999 | Brown et al. |
| 5,897,493 A | 4/1999 | Brown |
| 5,899,855 A | 5/1999 | Brown |
| 5,910,107 A | 6/1999 | Iliff |
| 5,911,687 A | 6/1999 | Sato et al. |
| 5,913,310 A | 6/1999 | Brown |
| 5,918,603 A | 7/1999 | Brown |
| 5,931,791 A | 8/1999 | Saltzstein et al. |
| 5,933,136 A | 8/1999 | Brown |
| 5,935,060 A | 8/1999 | Iliff |
| 5,951,300 A | 9/1999 | Brown |
| 5,960,403 A | 9/1999 | Brown |
| 5,985,559 A | 11/1999 | Brown |
| 5,987,519 A | 11/1999 | Peifer et al. |
| 5,997,476 A | 12/1999 | Brown |
| 6,007,493 A | 12/1999 | Ericksen et al. |
| 6,022,315 A * | 2/2000 | Iliff .......................... 600/300 |
| 6,032,119 A | 2/2000 | Brown et al. |
| 6,045,513 A | 4/2000 | Stone et al. |
| 6,071,236 A | 6/2000 | Iliff |
| 6,080,106 A * | 6/2000 | Lloyd et al. ................. 600/300 |
| 6,113,540 A | 9/2000 | Iliff |
| 6,167,362 A | 12/2000 | Brown et al. |

\* cited by examiner-

FIG. 19

| Health Check Score | | |
|---|---|---|
| Question | Symptom | Value |
| Above: (Maximum Allowed Weight + Trigger Weight Change) | Fluid accumulation | 10 |
| Are you feeling more short of breath? | Dyspnea | 7 |
| Are you coughing more than usual? | Congestion in the lungs | 3 |
| Are your ankles or feet more swollen? | Pedal edema | 5 |
| Does your stomach feel more bloated? | Stomach edema | 3 |
| Having more chest discomfort (angina)? | Chest discomfort (angina) | 7 |
| Are you urinating less than usual? | Urinating Less | 5 |
| Are you more tired than usual? | Fatigue | 2 |
| Do you feel dizzy or lightheaded? | Hypotension | 5 |
| Are you taking all your medication? | Medication compliance | 7 |
| Are you reducing your sodium | Sodium intake | 1 |
| Did you exercise yesterday? | Fitness | 1 |

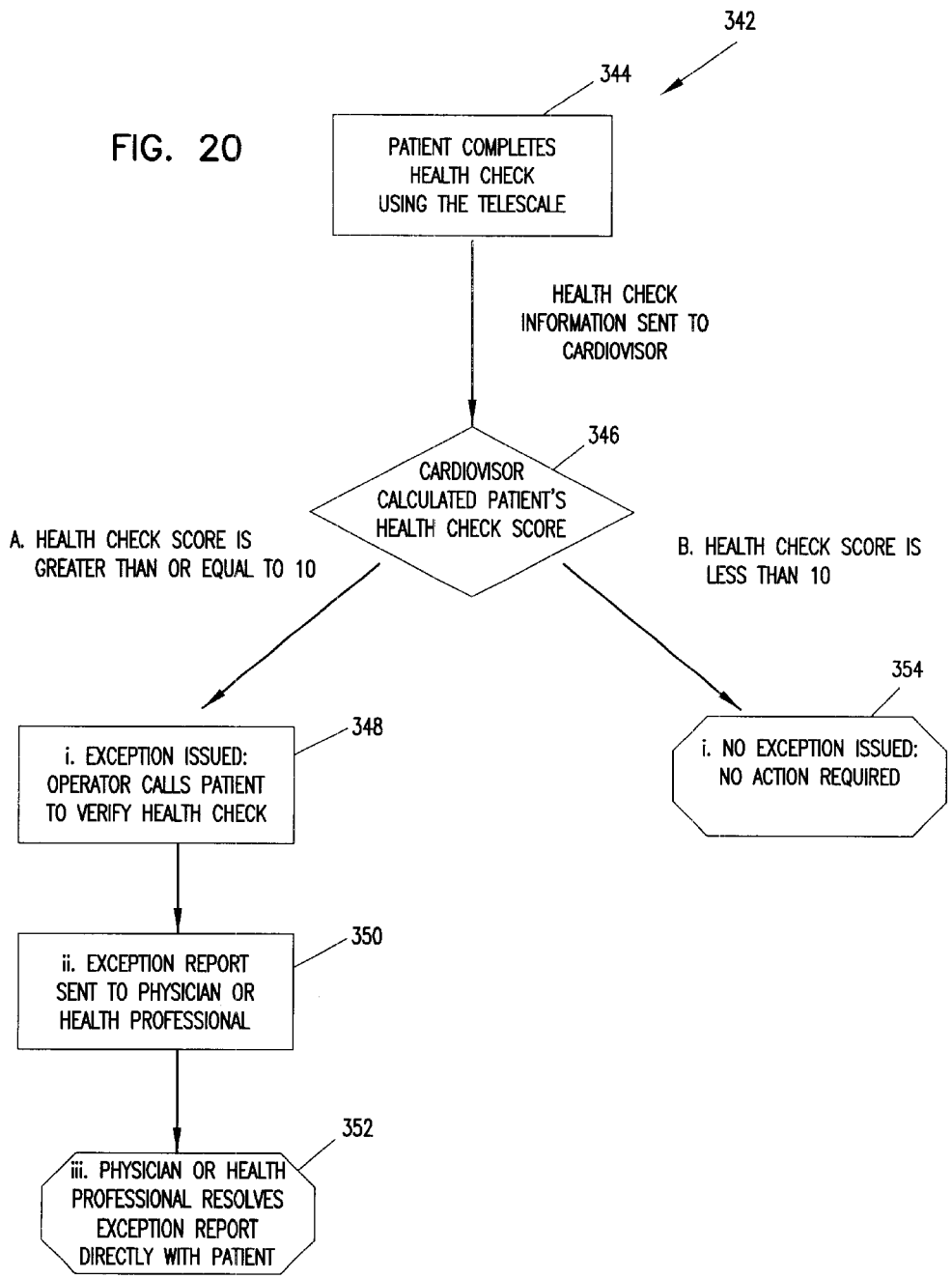

MEDICAL WELLNESS PARAMETERS MANAGEMENT SYSTEM, APPARATUS AND METHOD

This Application relates to co-pending application Ser. No. 09/293,619, Titled "Apparatus and Method for Monitoring and Communicating Wellness Parameters of Ambulatory Patients," which, in its entirety, is herein incorporated by reference.

BACKGROUND

There is a need in the medical profession for a medical wellness parameters management system, apparatus and method capable of monitoring and transmitting physiological and wellness parameters of ambulatory patients to a remote central computer site where a medical professional caregiver evaluates such physiological and wellness parameters. Specifically, there is a need for an interactive apparatus that is in communication with a remote central computer coupled to a database, the central computer also being in communication with a plurality of workstations, such that a medical professional caregiver can manage, supervise and provide medical treatment to remotely located ambulatory patients.

There is needed a system including an apparatus that monitors and transmits physiological and wellness parameters of ambulatory patients to a remote computer, whereby the wellness parameters are evaluated and stored in a main database. There is also needed as part of the system a plurality of workstations located remote from the central computer whereby a medical professional caregiver enters data into the database and evaluates reports issued by the central computer and provokes better overall health care and treatment for the patient. Accordingly, such a system can be used to prevent unnecessary hospitalizations of such ambulatory patients.

Patients suffering from chronic diseases, such as congestive heart failure, will benefit from such home monitoring apparatus. These patients normally undergo drug therapy and lifestyle changes to manage their medical condition. In these patients, the medical professional caregiver monitors certain wellness parameters and symptoms including: weakness, fatigue, weight gain, edema, dyspnea (difficulty breathing or shortness of breath), nocturnal cough, orthopnea (inability to lie flat in bed because of shortness of breath), and paroxysmal nocturnal dyspnea (awakening short of breath relieved by sitting or standing); body weight to measure the response of drug therapy; oxygen saturation levels; blood pressure; and heart rate. Patients will also benefit from daily reminders to take medications (improving compliance), reduce sodium intake and/or perform some type of exercise. With the information received from the monitoring device, the medical professional caregiver can determine the effectiveness of the drug therapy, the patient's condition, whether the patient's condition is improving or whether the patient requires hospitalization or an office consultation to prevent the condition from getting worse.

Accordingly, there is needed a system, apparatus and method for monitoring the patients from a remote location, maintaining a database of wellness parameters and communicating with workstations located at clinics, hospitals, emergency rooms located remote from the central computer and Health Maintenance Organizations (HMOs). Thus, allowing medical professional caregivers to monitor and manage a patient's condition to reduce hospitalizations by early identification of symptoms and weight changes to prevent unnecessary hospitalizations and office visits and providing immediate feedback of a patient's status thus allowing medication and fluid adjustments to be made over the telephone.

There also needed a system, apparatus and method to allow medical professional caregivers to decrease management expenses and manage patient's more efficiently by utilizing automatic symptom and weight variance identification and thereby directing attention only to patients in need of assistance. There is also needed a system that that issues comprehensive exception reports providing 21-day symptom, weight, and hospitalization information; current medication list with dosage and frequency; and descriptive operator comments.

Furthermore, there is needed a system, apparatus and method that issues trend reports for any period of a patient or group of patients' enrollment. Thus allowing a medical professional caregiver to select from reports on: weight, symptoms, hospitalizations and emergency room visits.

The patient receives the benefits of improved health when the professional caregiver is able to monitor and quickly react to any adverse medical conditions of the patient or to any improper responses to medication. Also, society benefits because hospital resources will not be utilized unnecessarily.

As a group, patients suffering from chronic diseases, such as congestive heart failure, are the most costly to treat. There are approximately 5 million patients in the U.S.A. and 15 million worldwide with chronic diseases, such as congestive heart failure. The mortality rate of patients over 65 years of age is 50%. Of those that seek medical help and are hospitalized, 50% are rehospitalized within 6 months. Of these, 16% will be rehospitalized twice. The patients that are hospitalized spend an average of 9.1 days in the hospital at a cost of $12,000.00 for the period. Accordingly, there is a need to reduce the rehospitalization rate of congestive heart failure patients by providing improved in-home patient monitoring, such as frequently monitoring the patient's body weight and adjusting the drug therapy accordingly.

Approximately 60 million American adults ages 20 through 74 are overweight. Obesity is a known risk factor for heart disease, high blood pressure, diabetes, gallbladder disease, arthritis, breathing problems, and some forms of cancer such as breast and colon cancer. Americans spend $33 billion dollars annually on weight-reduction products and services, including diet foods, products and programs.

For the foregoing reasons, there is a need for a management system, apparatus and method capable of monitoring and transmitting physiological and wellness parameters of ambulatory patients to a remote central computer site where a medical professional caregiver or case manager evaluates such physiological and wellness parameter and provides treatment accordingly.

SUMMARY

To overcome the limitations in the prior art described above and to overcome other limitations that will become apparent upon reading and understanding the present specification, the system, method, apparatus and article of manufacture having features of the invention provide a medical system, method, apparatus and article of manufacturing for monitoring and managing one or more ambulatory patients on a computer and allowing a caregiver to review the ambulatory patients' wellness parameters to provide treatment in accordance with the wellness parameter.

In accordance with one embodiment of the invention, a medical system for monitoring and managing one or more ambulatory patients on a computer and allowing a caregiver to review the ambulatory patients' wellness parameters to provide treatment in accordance with the wellness parameters is provided. The system includes, a patient monitoring apparatus having a first communication device associated therewith for monitoring a patient's wellness parameters. A central computer located remote from the monitoring apparatus and in communication therewith, the central computer having a second communication device associated therewith for communicating wellness parameters and treatment data over a communications link established between the central computer and the monitoring apparatus, the central computer being operated for querying the patient via the patient monitoring apparatus, receiving and processing measured wellness parameters from the monitoring apparatus and calculating a score according to the wellness parameters. A main database coupled to the central computer having patient medical records stored therein and one or more computer workstations located remote from the central computer and in communication therewith, the one or more computers having a third communication device associated therewith for communicating physical examination data between the central computer and the one or more workstations over a communication link established therebetween. The score calculated by the central computer according to the wellness parameters is compared with a predetermined value, and based on the results of the comparison the central computer issuing an exception report and communicating the exception report to the one or more workstations located remote therefrom, whereby a caregiver located at the remote workstation site is notified of the exception report.

In accordance with another embodiment of the invention, a method for monitoring and managing one or more ambulatory patients on a computer and allowing a caregiver to review the ambulatory patients' wellness parameters to provide treatment in accordance with the wellness parameters is provided. The method includes receiving a patient's wellness parameters at a central computer from a patient monitoring apparatus located remote therefrom, creating a patient medical record in a database coupled to the central computer and storing the patient's wellness parameters received from the monitoring apparatus into the database, monitoring the patient's status, calculating a score with the central computer based on the patient's wellness parameters, comparing the score with a predetermined value and based on the results of the comparison, issuing an exception report and communicating the exception report to one or more workstations located remote from the central computer, whereby a caregiver is notified of the exception report.

In accordance with a further embodiment of the invention, an apparatus for monitoring and managing one or more ambulatory patients on a computer and allowing a caregiver to review the ambulatory patients' wellness parameters to provide treatment in accordance with the wellness parameters is provided. The apparatus includes a central computer located remote from a patient monitoring apparatus and in communication therewith, the central computer having a communication device associated therewith for communicating wellness parameters and treatment data over a communications link established between the central computer and the monitoring apparatus, the central computer being operated to query the patient via the patient monitoring apparatus, receiving and processing measured wellness parameters from the monitoring apparatus and calculating a score according to the wellness parameters received by the computer system, the computer system having one or more storage devices coupled thereto. The apparatus further includes one or more computer programs, performed by the central computer for receiving a patient's wellness parameters at a central computer from a patient monitoring apparatus located remote therefrom, creating a patient medical record in a database coupled to the central computer and storing the patient's wellness parameters received from the monitoring apparatus into the database, monitoring the patient's status, calculating a score with the central computer based on the patient's wellness parameters, comparing the score with a predetermined value and based on the results of the comparison, issuing an exception report and communicating the exception report to one or more workstations located remote from the central computer, whereby a caregiver is notified of the exception report.

In accordance with yet another embodiment of the invention, an article of manufacture comprising a computer program carrier readable by a computer system having one or more processors and embodying one or more instructions executable by the computer system to perform a method for monitoring and managing one or more ambulatory patients on a computer and allowing a caregiver to review the ambulatory patients' wellness parameters and provide treatment in accordance with the wellness parameters is provided. The method includes receiving a patient's wellness parameters at a central computer from a patient monitoring apparatus located remote therefrom, creating a patient medical record in a database coupled to the central computer and storing the patient's wellness parameters received from the monitoring apparatus into the database, monitoring the patient's status, calculating a score with the central computer based on the patient's wellness parameters, comparing the score with a predetermined value and based on the results of the comparison, issuing an exception report and communicating the exception report to one or more workstations located remote from the central computer, whereby a caregiver is notified of the exception report.

BRIEF DESCRIPTION OF THE DRAWINGS

Referring now to the drawings in which like reference numbers represent corresponding parts throughout:

FIG. 19 is one example of a diagram of health check score in accordance with the invention;

FIG. 20 is one example of a patient monitoring process in accordance with the invention.

DETAILED DESCRIPTION

In the following description, reference is made to the accompanying drawings that form a part hereof and that illustrate a specific embodiment in which the invention may be practiced. It is to be understood that other embodiments may be utilized as changes may be made without departing from the scope of the present invention.

System Description

Figure 1:
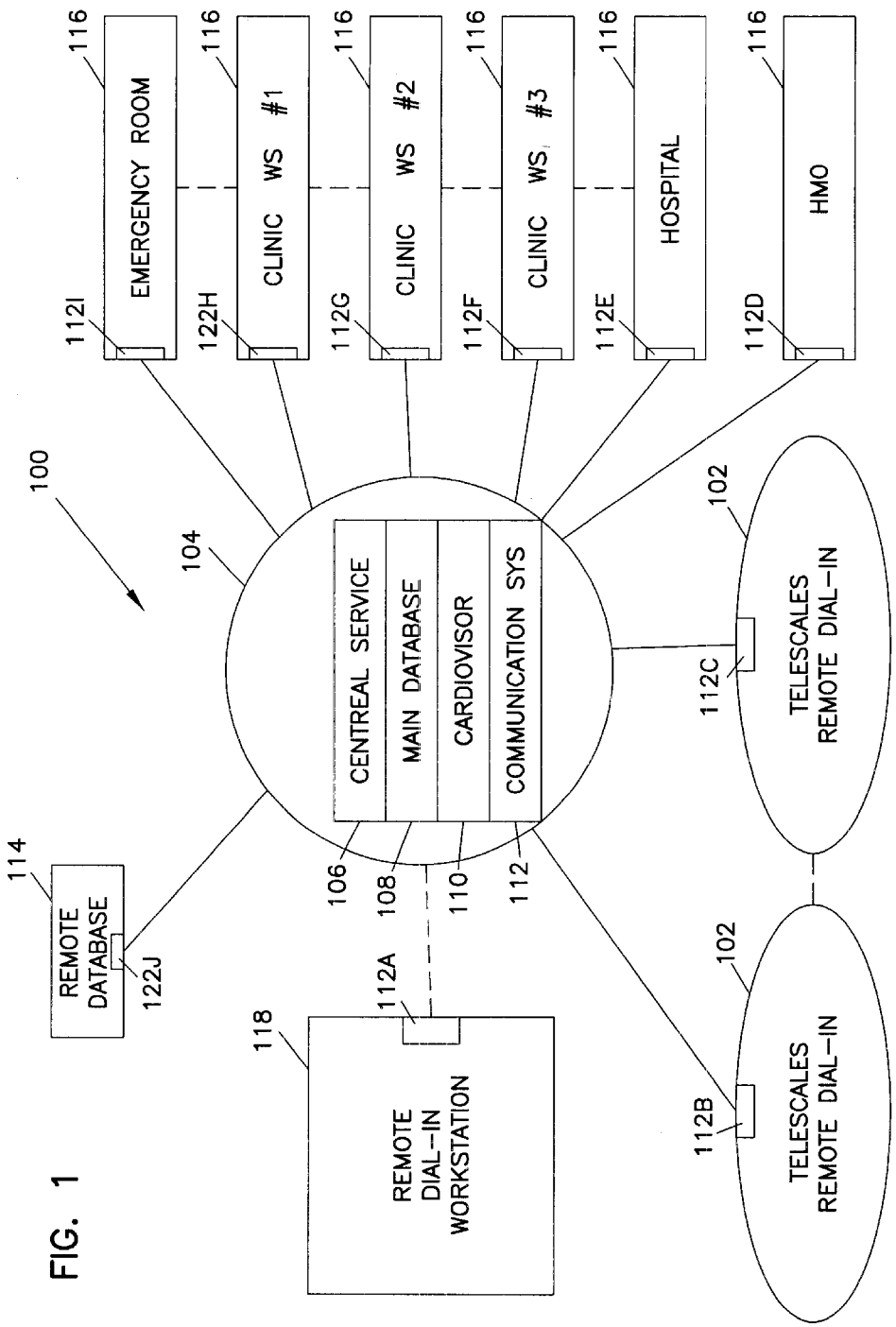
FIG. 1 illustrates one example of a system in accordance with the invention.

FIG. 1 illustrates a high level view of a system in accordance with the principles of the present invention. The system 100 includes one or more patient home monitoring apparatuses 102 (e.g., a TELESCALE™) and a central computer system 104 including a central server 106, database 108, software (e.g., the CARDIOVISOR™) 110 and communication system 112. Furthermore, the system provides communication capabilities between the central computer system 104, the home monitoring apparatus 102, other databases located remote 114 from the central computer system 104, other computers 116 (e.g., workstations) located remote from the central computer system 104, such locations including one or more: medical clinics, hospitals, emergency rooms, HMOs and the like. The system 100 also provides for dial-in capabilities from a remote dial-in workstation 118 located remote from the central computer system 104 for allowing a medical professional caregiver at workstation 116 or remote dial-in workstation 118 to access to patient information stored in the database 108.

One skilled in the art will appreciate that communication devices 112A may be used for communicating between the remote dial-in workstation 118 and the communication system 112 of the central computer system 104. Similarly communication devices 112B–C may be used for communicating between the home monitoring apparatuses 102 and the communication system 112 of the central computer system 104. Also, communication devices 112D–I may be used to communicate information between the other computers 116 (e.g., workstations) and the communication system 112 of the central computer system 104. Furthermore, it will be appreciated that communication device 112J may be used to communicate between the remote database 114 and the communication system 112 of the central computer system 104. It will also be appreciated by those skilled in the art that the communication system 112 of the central computer system 104 may include one or more communication devices.

Figure 2:
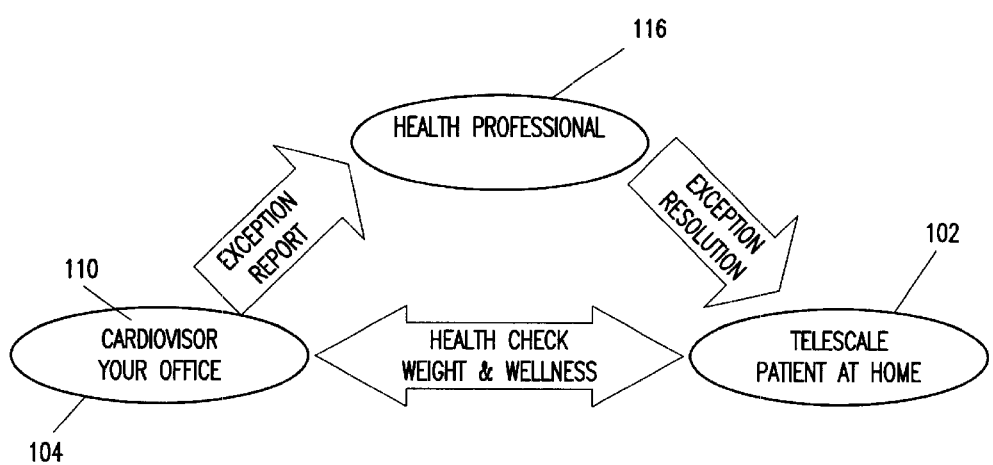
FIG. 2 illustrates one example of an information flow diagram in accordance with the invention.

FIG. 2 illustrates a high level information flow diagram between a patient in the home using a home monitoring apparatus 102, a system user executing software 110, and a medical professional caregiver. The patient home monitoring apparatus 102 transmits and receives information from the central computer system 104. Likewise, the central computer system 104 transmits and receives information from the patient home monitoring apparatus 102. Also, the central computer system 104 issues exception reports if certain patient wellness parameters fall outside a predetermined value. The exception report may be transmitted to a workstation 116 of a medical professional caregiver located remote from the central computer system 104. Alternatively, the exception report may be evaluated by a medical professional caregiver at the central computer 104 site. In either case, the medical professional caregiver evaluates the exception report and addresses the patient's symptom(s) that contributed to triggering the exception report.

Accordingly, a system 100 according to the principles of the present invention provides an effective, efficient, and easy to use Congestive Heart Failure (CHF) monitoring and management tool. The system 100 allows a medical professional caregiver to monitor patients in their home from a remote location (e.g., the caregiver's office) by tracking weight and wellness information. The system provides the medical professional caregiver with an early indication of patient symptoms and weight changes. This information allows the medical professional caregiver to adjust medication and fluid intake by telephone which may prevent unnecessary hospitalizations and emergency room visits.

In one embodiment, a system 100 in accordance with the invention, can reduce unnecessary hospitalizations, emergency room visits and doctor's office visits by early identification of symptoms and weight changes. Furthermore, the system 100 can provide immediate feedback of the patient's status and thus allowing medication and fluid adjustments to made by telephone. Moreover, the system can decrease management expenses and help the medical professional caregiver manage patients more efficiently since the automatic symptom and weight variance identification directs the caregiver's attention only to patients in need of assistance.

In one embodiment, the system 100 in accordance with the present invention provides comprehensive "Exception Reports." The exception reports provide: 21-day symptom, weight and hospitalization information; current medication list with dosage and frequency; and descriptive operator comments.

In one embodiment, the system 100 in accordance with the present invention provides trend reports for any period of a patient or group of patients' enrollment. The trend reports may be selected according to weight, symptoms, hospitalizations and/or emergency room visits.

The Patient Home Monitoring Apparatus

Figure 3A:
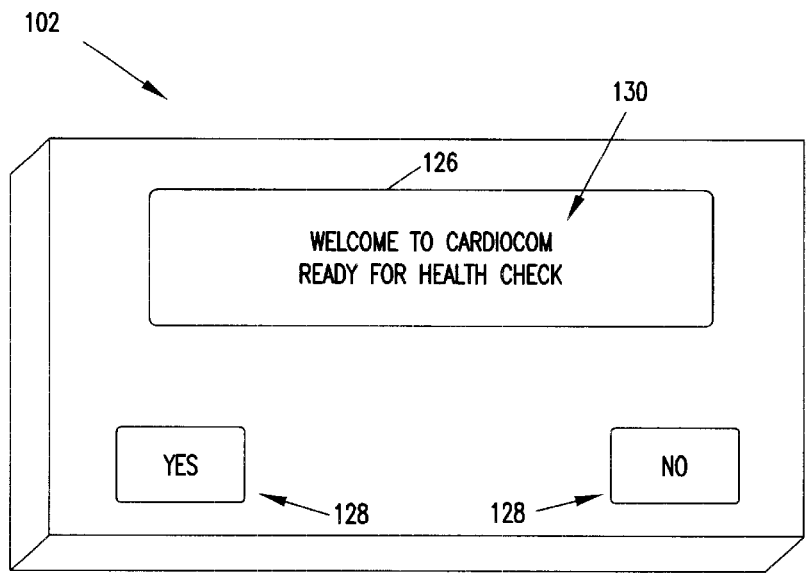
FIGS. 3A–B illustrate one example of a diagram of a patient home monitoring apparatus.
Figure 3B:
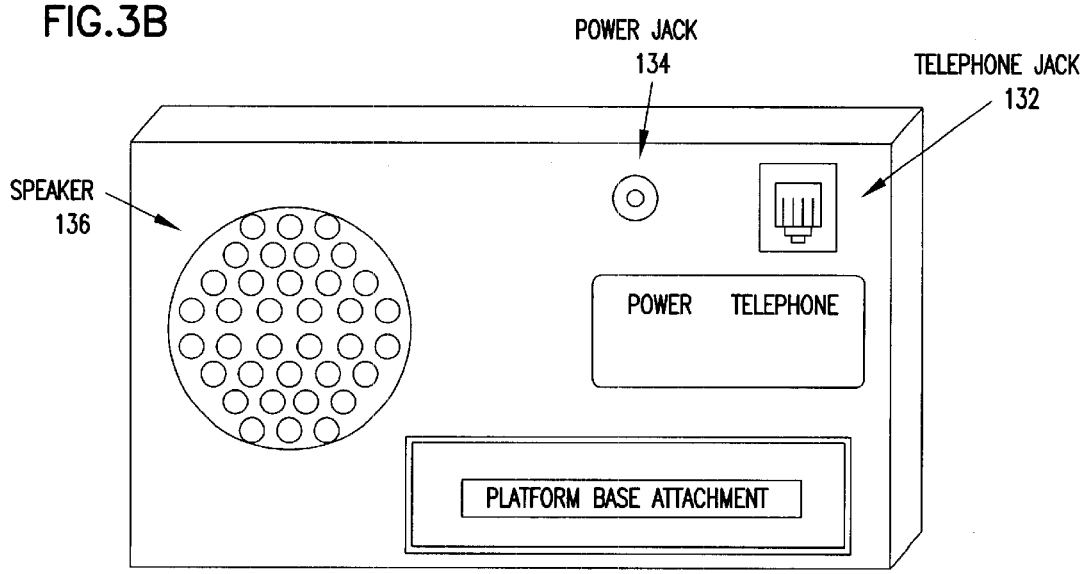

FIG. 3 illustrates a diagram of one example of a patient home monitoring apparatus 102, a patient home monitoring apparatus. A more detailed description of the patient home monitoring apparatus 102 is provided in co-pending application Ser. No. 09/293,619, Titled "Apparatus and Method for Monitoring and Communicating Wellness Parameters of Ambulatory Patients," which, in its entirety, is herein incorporated by reference.

In one embodiment, the patient home monitoring apparatus 102 is a device used to collect a patient's weight and wellness information using a protocol referred to as the HEALTH CHECK. The patient home monitoring apparatus 102 automatically transmits this information from the patient's home to the software 110 over a communications link established therebetween (e.g., a telephone line).

The patient home monitoring apparatus 102 includes a medical grade scale integrated with a modem, microprocessor and wellness parameter monitor (not shown). Some example features of the patient home monitoring apparatus 102 are a display 126; ergonomic; waist-height user interface; large, extra bright, easy to read display; easy-touch, large "Yes" and "No" buttons 128; clear, friendly voice; and volume selectable ON/OFF.

In one embodiment, the patient home monitoring apparatus 102 provides a sturdy platform; consistent and accurate weight measurement; medical grade, calibrated, electronic scale; and modem design.

Using the Patient Home Monitoring Apparatus

In one embodiment, a patient home monitoring apparatus 102 (e.g., the TELESCALE™) outputs a message 130 such as "Welcome to Cardiocom. Ready for Health Check?" on the output display device 126. A patient will then proceed by selecting "Yes" or "No" on the touch pad 128. If the patient selects "Yes," the Health Check will begin. Note that the patient need not step on the scale (not shown) to answer the questions. If the patient selects "No," the patient home monitoring apparatus 102 will function as a scale only and will not transmit the reading. If the patient has selected "Yes," the patient will then answer a series of twelve Health Check questions (listed below) by pressing "Yes" or "No" on the key pad. An example list of questions that the patient may be queried on are as follows:

1) Are you feeling short of breath?
2) Are you coughing more than usual?
3) Are your ankles or feet swollen?
4) Does your stomach feel bloated?
5) Having more chest discomfort (angina)?
6) Are you urinating less than usual?
7) Are you more tired than usual?
8) Do you feel dizzy or lightheaded?
9) Are you taking your medication?
10) Are you reducing your sodium?
11) Did you exercise yesterday?

During the Health Check procedure, the patient will also be asked to weigh him/herself. Accordingly, the patient will be asked to step off the patient home monitoring apparatus 102 so it can "auto-zero." At which time the message "000.0 lbs." will appear on the output display 126. Then, the patient will be asked to step on the patient home monitoring apparatus 102. Next, the patient home monitoring apparatus 102 will display the patient's:

1) Current Weight (e.g., 155.0 lbs.);
2) Variance to Prior Day's Weight (e.g., gained 1.0 lbs.);
3) Maximum Allowed Weight (e.g., 150.0 lbs.);
4) Variance of Maximum Allowed Weight (e.g., exceeded Maximum Allowed Weight by 5.0 lbs.)

The Health Check is now complete and a message "Do you need to revise your answers?" will appear. This gives the patient an opportunity to revise any incorrect answers before transmission to the central computer system 104. If "No" is selected (e.g., no revisions), the data will be transmitted to the central computer system 104 and the message "Thank you. Have a good day!" then "Your data is being transmitted" will appear on the display 126. If revisions are required and "Yes" is selected, the Health Check will be repeated. All data gathered from the initial Health Check will be deleted and the patient must repeat the Health Check as specified in steps 1–4.

In one embodiment, the home monitoring apparatus 102 is not limited to being located in the patient's home. For example, the patient may take their patient home monitoring apparatus 102 with them when they travel. However, the telephone number that the patient home monitoring apparatus 102 uses to call the central computer system 104 may have to be modified. In order to change the telephone number, the patient must first connect the patient home monitoring apparatus 102 to a telephone outlet via a telephone-jack 132, then press and hold the "No" button and plug-in the power supply in the power jack 134 of the patient home monitoring apparatus 102 at the same time. Accordingly, the patient home monitoring apparatus 102 will then display the central computer system 104 telephone number and ask the patient if they want to change the central computer system's 104 telephone number. The patient then needs to press "Yes," then the patient home monitoring apparatus 102 will ask if an Area Code is required (patient will press "Yes" if required). The patient home monitoring apparatus 102 will then ask if the number should begin with a "1" for long distance (patient will press "Yes" if required). The Health Check will appear and the patient home monitoring apparatus 102 will dial the software 110 according to the directions specified.

In one embodiment, the patient home monitoring apparatus 102 communicates with the patient using a synthesized electronic voice audible through speaker 136. The patient may turn the sound "OFF" or "ON." To do so when the message "Welcome to Cardiocom, Health for Health Check" is displayed, the patient should press and hold the "No" button for 3 seconds. The TELESCALE™ will then ask "Do You Want the Sound Turned 'ON'?" Accordingly, the patient makes the desired selection.

In one embodiment of the invention, the home monitoring apparatus is shipped to a patient having a predetermined telephone number stored in a memory circuit of the home monitoring apparatus. In use, when a patient first applies power or uses the home monitoring apparatus while coupled to a telephone line, the home monitoring apparatus automatically dials the predetermined number and establishes communication with a central computer located remote therefrom. At such time, the central computer queries a database coupled thereto and determines the appropriate telephone number that the home monitoring apparatus is to call into. This may include the telephone which clinic, hospital, emergency room or HMO. The central computer then downloads the appropriate telephone number to the home monitoring apparatus. The appropriate telephone number is then stored in the memory of the home monitoring apparatus. Accordingly, when the home monitoring apparatus is used it will dial the appropriate telephone number.

Although one specific example of a patient home monitoring apparatus 102 has been described for purposes of illustration, those skilled in the art will appreciate that other patient home monitoring apparatuses may be employed without departing from the scope and spirit of the present invention.

The Central Computer System

One embodiment of the present invention provides a central computer system 104 (e.g., the CARDIOVISOR™) located remote from the home monitoring apparatus 102. In accordance with the principles of the present invention, the central computer system 104 includes a customized central server 106 and proprietary software system 110 that receives the patient's weight and wellness information from a patient home monitoring apparatus 102 (e.g., the TELESCALE™). The central computer system 104 may be used to enter and update a medical professional caregiver's (e.g., a physician) and a patient's records; monitor patient status; issue exception reports; and issue trend reports.

Hardware Environment

Figure 4:
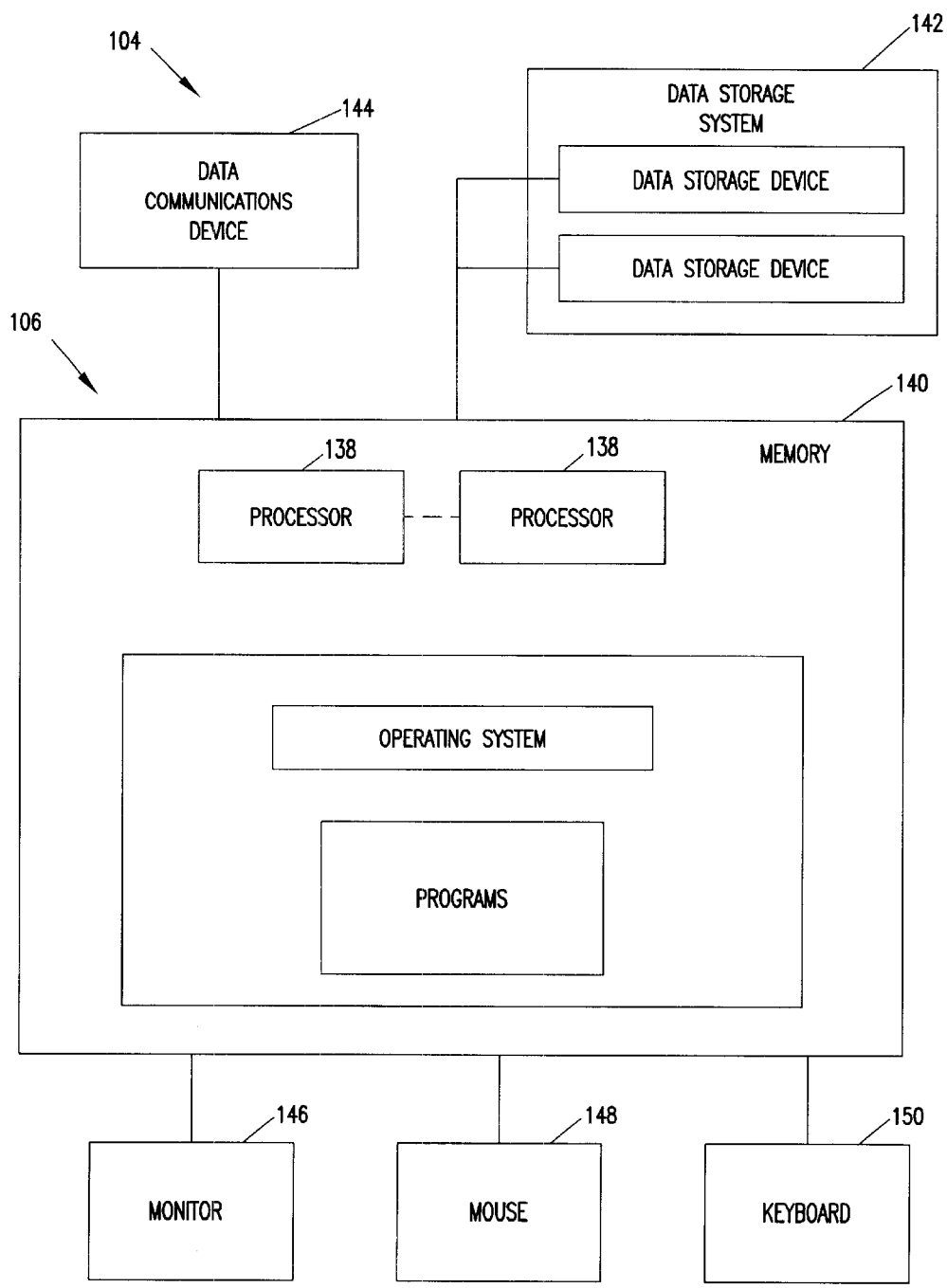
FIG. 4 is one example of a diagram of a hardware environment that may be used to implement one embodiment of the invention.

FIG. 4 is a diagram of a hardware environment that may be used to implement one embodiment of the invention. The present invention may be implemented using a central server 106, which generally includes, inter alia, one or more processors 138, random access memory (RAM) 140, a data storage system 142 including one or more data storage devices (e.g., hard, floppy and/or CD-ROM disk drives, etc.), data communications devices 144 (e.g., modems, network interfaces, etc.), monitor 146 (e.g., CRT, LCD display, etc.), mouse pointing device 148 and keyboard 150. It is envisioned that the central server 106 may be interfaced with other devices, such as read-only memory (ROM), video card, bus interface, speakers, printers, or any other device adapted and configured to interface with the central server 106 that is capable of providing an output from the central server. Those skilled in the art will recognize that any combination of the above components or any number of different components, peripherals and other devices may be used with the computer system. For example, the central server 106 may include an 8 channel MODEM; CD-ROM Back-up: CD-ReWritable, CD-Recordable Drive; and a 17 inch monitor. Those skilled in the art will also appreciate that computers and workstations 116 located remote from the central computer system will generally have a similar implementation as the central computer.

In one embodiment, a central server 106 may be provided with an 8 channel MODEM that allows up to eight patient home monitoring apparatus' 102 to simultaneously access and transmit Health Check information to the central computer system (e.g., CARDIOVISOR™). Each patient home monitoring apparatus 102 data transmission takes less than 25 seconds. The central server 106 can receive over 1,900 calls per hour. This high capacity call handling configuration makes it ideal for both small and large centers.

In one embodiment of the invention, the CD-ROM Back-up: CD-ReWritable, CD-Recordable Drive automatically stores a duplicate (back-up) copy of all patient and medical professional caregiver (e.g., physician) data on a compact disc (CD) each night. The CD can store approximately one year of patient data. A new CD should be installed each year. The used CD should be labeled and stored for future reference. In accordance with the principles of the invention, a database of patient and medical professional caregiver (e.g., physician) data is updated, maintained and managed by the central computer system.

The Central Computer Software

In one embodiment of the invention, the features of the central computer's software (e.g., CARDIOVISOR™) include an operator logon; patient and medical professional caregiver records, entry and edit; patient monitoring; exception resolution; issuing exception reports; and issuing trend reports.

Figure 5A:
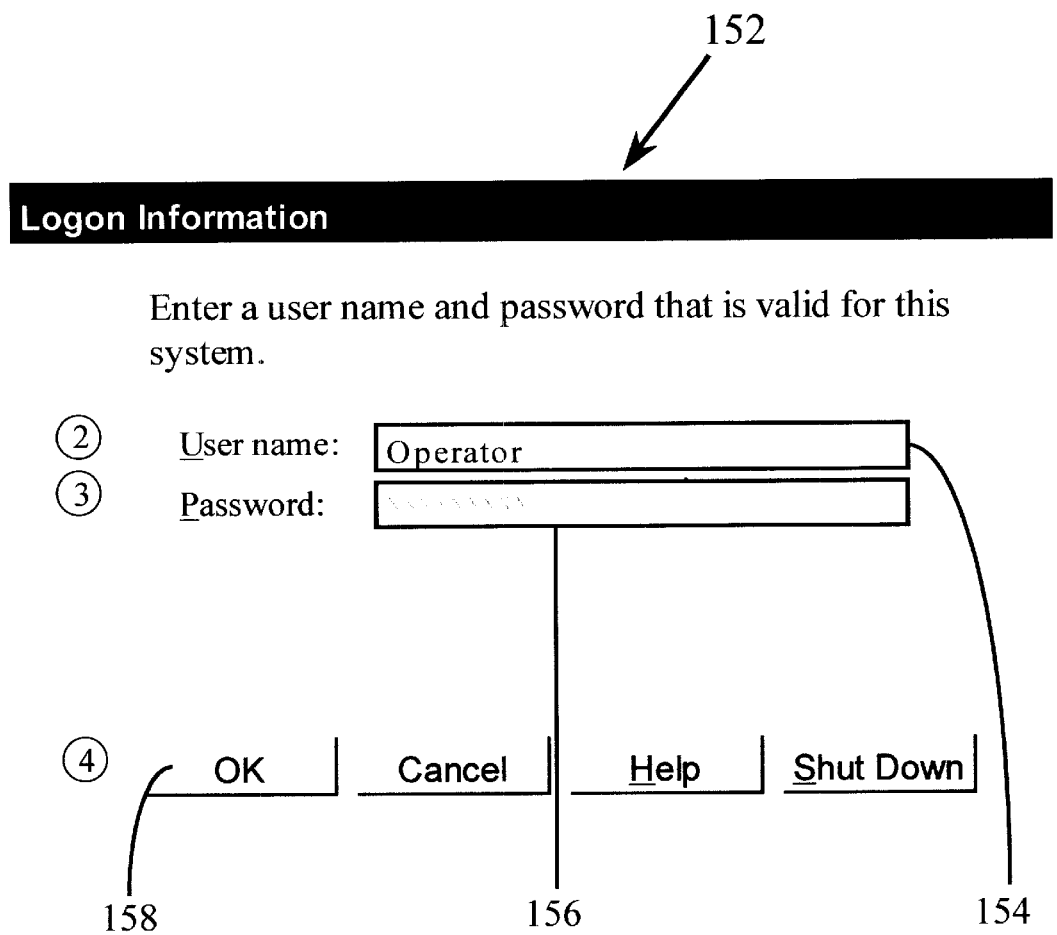
FIG. 5A is one example of a computer user interface logon screen in accordance with the invention.
Figure 5B:
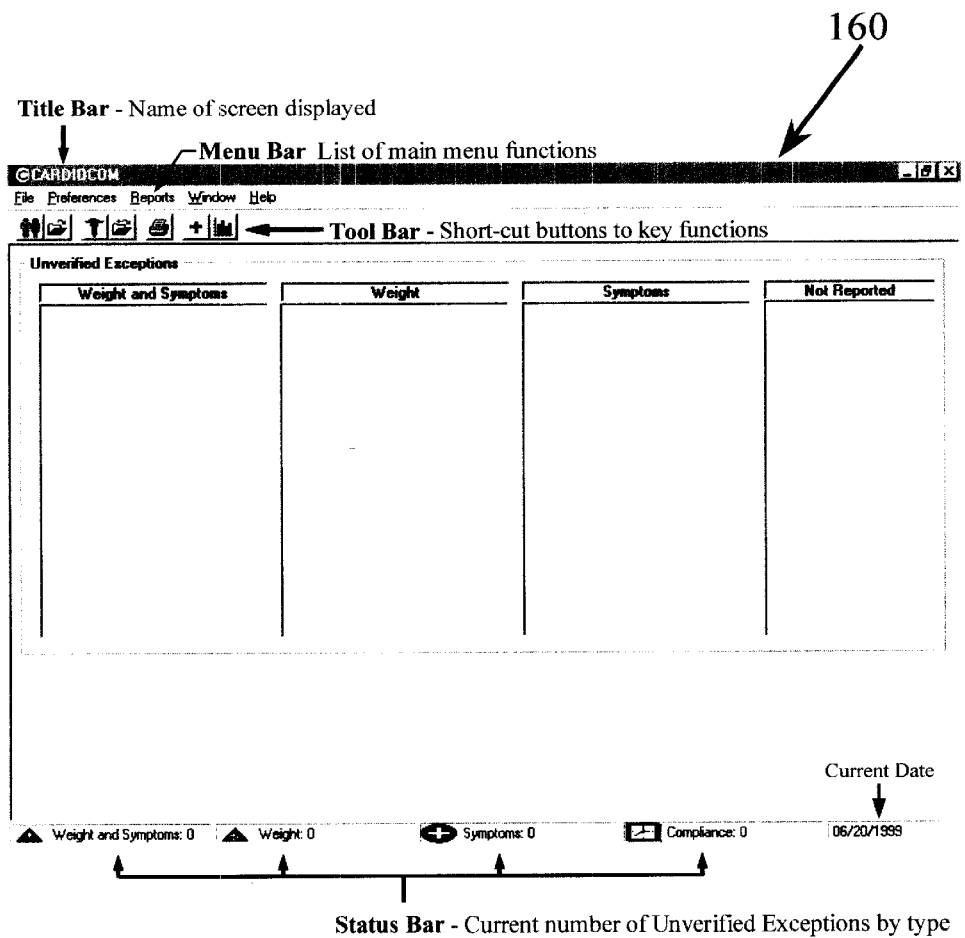
FIG. 5B is one example of a computer user interface screens in accordance with the invention.

FIG. 5A illustrates one embodiment of the invention, the logon feature provides the user with a protected user name and password to prevent unauthorized users from operating the System. To initiate a logon procedure the user simultaneously presses the Ctrl, Alt, Delete keys. Then, in the User box 154, the name Operator should appear. If the User name is blank, then the user should type in the word Operator. In the Password box 156, the user then types a word that identifies the system management organization. A series of x's will appear as you type in the word identifier to prohibit unauthorized users from seeing the password. Upon selecting OK 158 the software program will be loaded and the main screen 160 (FIG. 5B) (Unverified Exceptions) will appear.

Figure 6A:
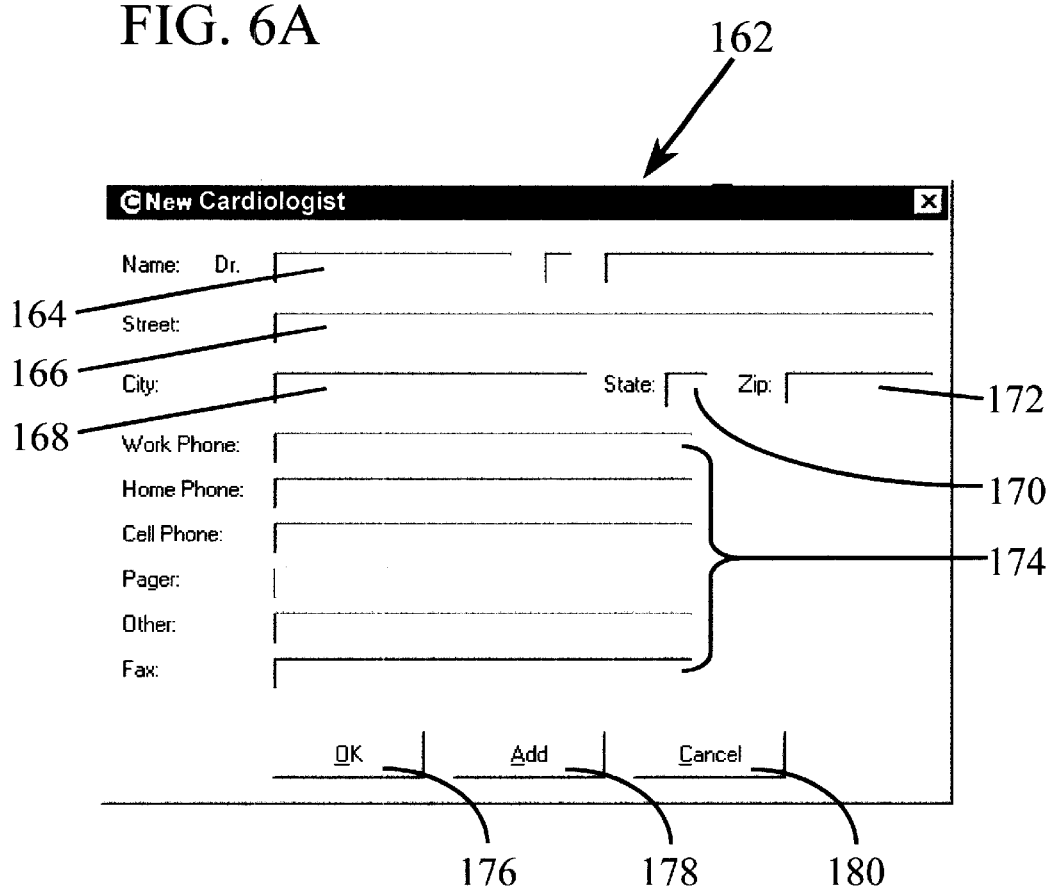
FIGS. 6A–B are examples of medical provider record computer user interface screens in accordance with the invention.
Figure 6B:
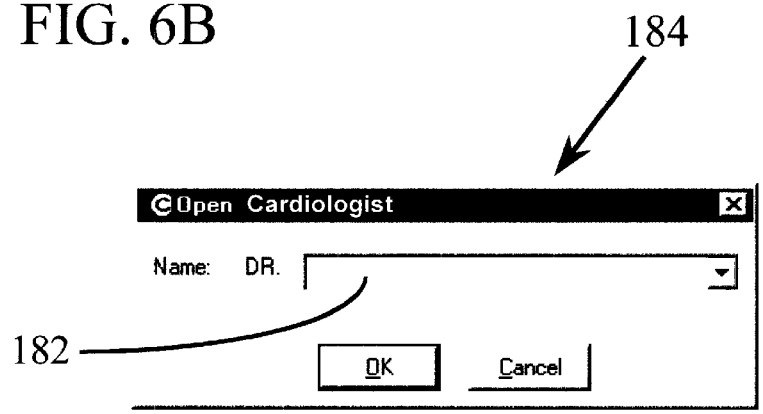

Those skilled in the art will appreciate that a toolbar including buttons that provide immediate access to frequently used commands and options may be provided to assist a system operator (or user) perform the patient monitoring, database management, etc. For example, the following functions may be executed by the user by clicking the appropriate icons embedded in the toolbar:

1) Open a New Patient Record
2) Edit an Existing Patient Record
3) Open a New Physician Record
4) Edit an Existing Physician Record
5) Print
6) View Exception Reports
7) View Trend Reports FIGS. 6A and 6B illustrate one embodiment of a user screen of the present invention, for performing the patient and medical professional caregiver record entry and edit function. A new "Physician Record" 162 is entered for each physician or health professional who will monitor patients and receive exception reports. The physician information in then entered in the appropriate fields. The following is an example of the information that may be entered in the Physician Record 162:

1) Name 164—First, Middle Initial, and Last Name
2) Street 166—Address including Street, Apartment, Suite, etc.;
3) City 168, State 170, Zip 172—City, State (2 letter abbreviation), and Zip; and
4) Phone 174—Work, Home, Cellular, Pager, Other and Fax numbers.

The user may then either return to the main menu or enter another physician record. The user presses OK 176 to enter the physician's record into the database 108 and return to the main menu. Alternatively, the user may then presses Add 178 to enter the physician's record into the database 108 and continue entering additional physician records. At any time the user may press Cancel 180 to stop and return to the main menu. Accordingly, no information will be entered.

To edit a Physician Record a user may select File, Open, Physician on the menu or may click on the appropriate icon. The user may then enter the physician's last name in the name box 182 or use the scroll-down menu 184 to locate a physician already contained in the database. Once the desired record is located, the user may select OK and the Edit Physician screen will be displayed. Accordingly, the user may then make any necessary changes in the physician record. Pressing OK will save the changes to the physician record. Pressing Cancel returns the user to the main menu.

Figure 7:
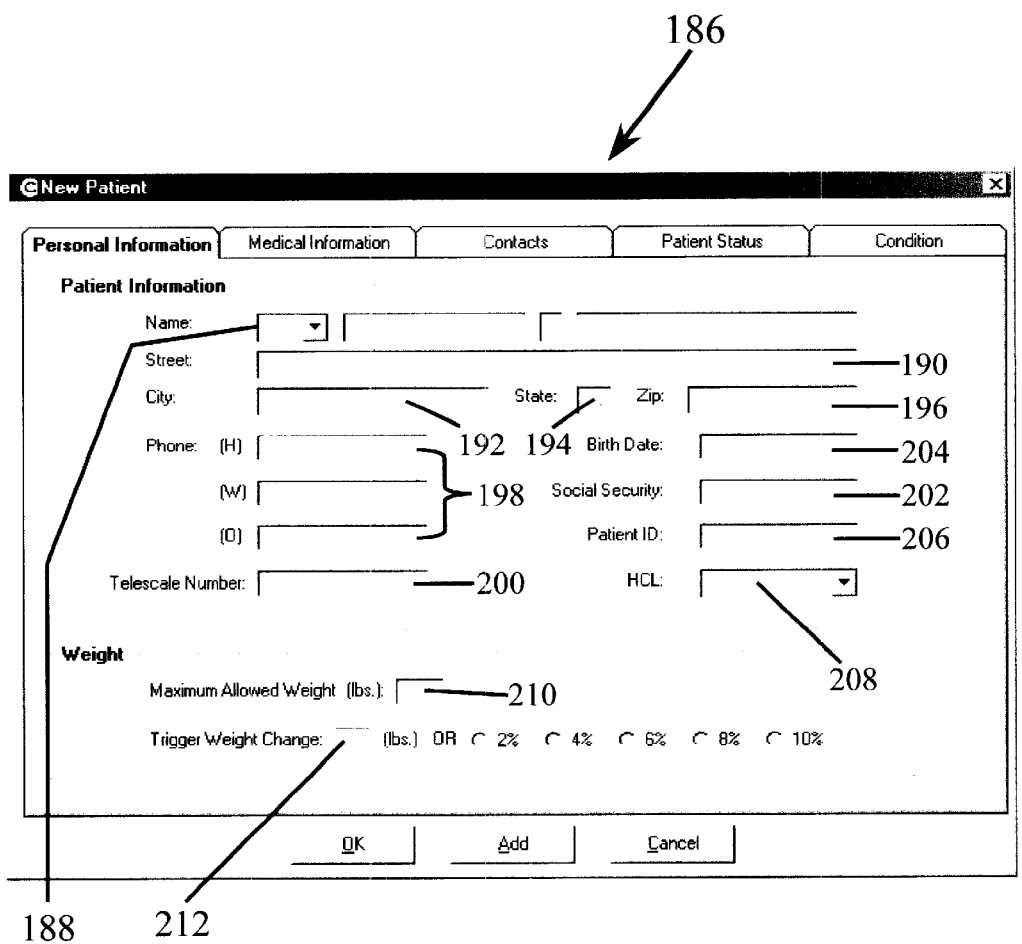
FIG. 7 is one example of a patient record computer user interface screen in accordance with the invention.

FIG. 7 illustrates one embodiment of a New Patient Record screen 186. To Enter a New Patient Record the user may select File, New, Patient on the menu bar or may click on the appropriate icon. The patient's Personal Information in then entered in the appropriate fields. The following is an example of the information that may be entered in the New Patient Record:

1) Name 188—Title, (Mr., Mrs., Ms., Dr.), First, Middle Initial, and Last Name;
2) Street 190—Address including Street, Apartment, Suite, etc.;
3) City 192, State 194, Zip 196—City, State (2 letter abbreviation), and Zip;
4) Phone 198—Home, Work and Other Numbers;

5) TELESCALE™ Number 200—patient monitoring apparatus 102 serial number assigned to the patent (located at the top, on the back of the patient monitoring apparatus 102, the patient is instructed to call the user with this number to activate their patient monitoring apparatus 102);

6) Social Security 202—9 digit Social Security number;

7) Birth Date 204—Month/Day/Year (e.g., Jan. 29, 1940);

8) Patient ID 206—The user may designate any number or text field; and

9) HCL 208—This may be any number or text field for which the user needs a pull-down menu. In some facilities this number may be used to identify the patient's clinic.

The user may then proceed to enter additional patient Personal Information including the weight information specified by the physician (e.g., a Cardiologist). This information is also entered in the appropriate fields. The following is an example of the additional information that may be entered in the patient's Personal Information Record:

1) Maximum Allowed Weight 210 (lbs.)—This is the weight (lbs.) that the patient is instructed not to exceed; and 2) Trigger Weight Change 212 (lbs.) OR (%)—This is the variance in weight from the Maximum Allowed Weight that will prompt an Exception. If the patient's weight is greater than or equal to the Maximum Allowed Weight plus the Trigger Weight Change, an Exception Report should be printed and sent to the physician.

The trigger Weight Change 212 may be entered in pounds (lbs.) or percent (%) of Maximum Allowed Weight.

Figure 8:
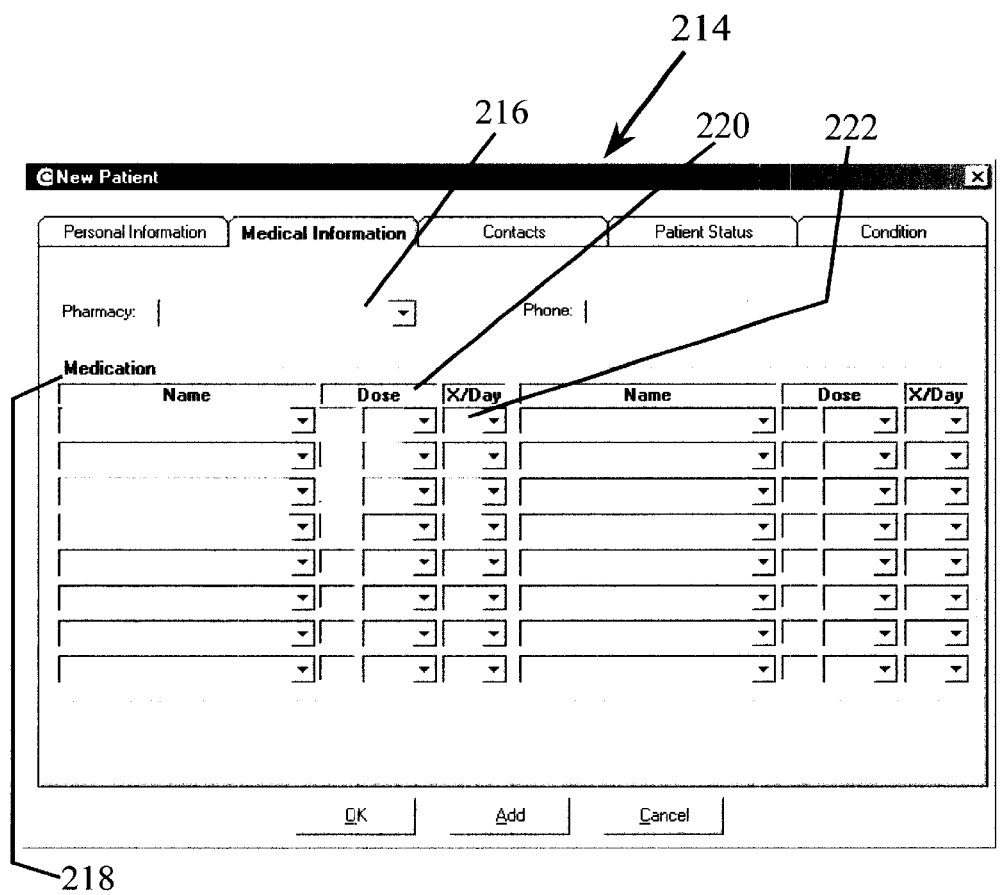
FIG. 8 is one example of a patient record computer user interface screen in accordance with the invention.

FIG. 8 illustrates one example of a patient's Medical Information screen 214. The user may then enter pharmacy 216 and medications 218 into the database 108. This information is also entered in the appropriate fields. The following is an example of the information that may be entered in the Medical Information Record:

1) Pharmacy 216—Name of patient's pharmacy and phone;

2) Medication 218—Patient's current medication as prescribed by the physician.

To enter the medication(s) in the patient record the user may then enter the medication Name using either the pull-down menu or manual entry. Medications may be permanently added to the pull-down menu by manually entering the medication name and following the instructions in the System. The user may then enter the medication Dose (e.g., 10 mg.) in corresponding dose field 220. Finally, the user may enter the medication frequency in X/day (e.g., 2) in the medication frequency field 222.

Figure 9:
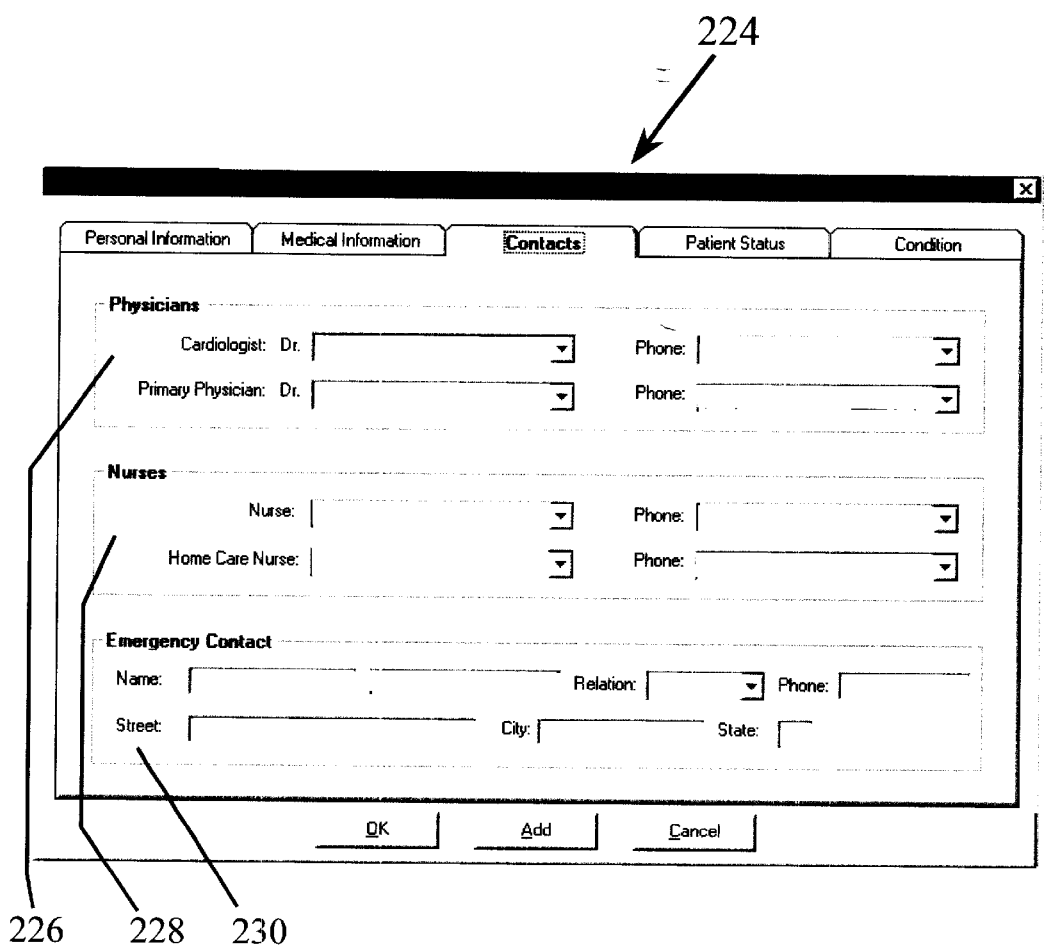
FIG. 9 is one example of a computer user interface screen in accordance with the invention.

FIG. 9 illustrates one example of a patient's Contact screen. For example, the user may then enter the patient's physician 226, nurses 228 and emergency 230 contacts. This information is also entered in the appropriate fields using either the pull-down menu or manual entry.

Figure 10:
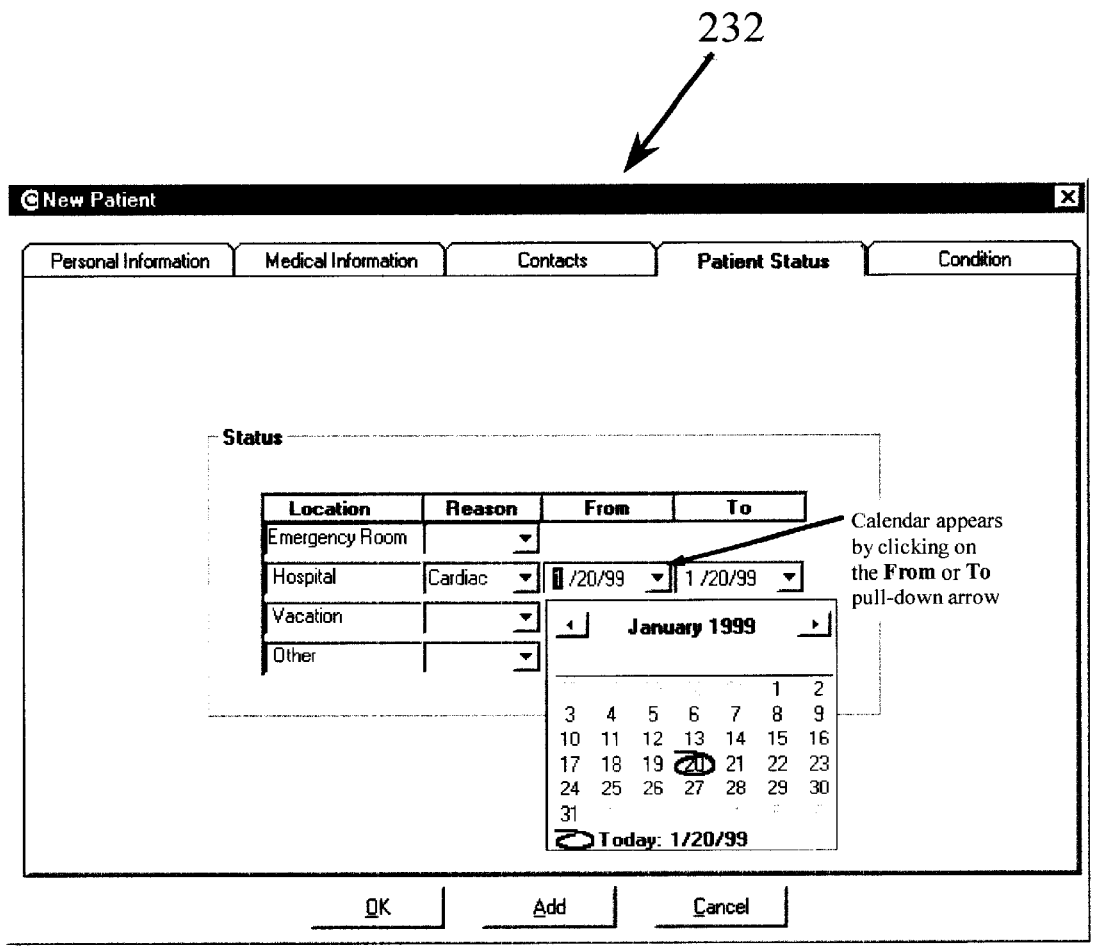
FIG. 10 is one example of a patient record computer user interface screen in accordance with the invention.

FIG. 10 illustrates one example of a Patient Status screen 232. This information is also entered in the appropriate fields. However, the Patient Status should be entered only if the patient will not be using the system immediately because he/she is in the Emergency Room, Hospital or on Vacation. The following is an example of how the Patient Status would be entered:

1) Identify the patient's Location;

2) Next to the selected location, enter the Reason by double-clicking on the field, and selecting one of the following: CHF, Cardiac, or Other;

3) Enter the dates the patient will be at the alternative location in the From and To fields. During this time period, Health Check information will not be reported;

4) The dates can be entered by clicking on the From and To field and using the pull-down menu to view the calendar. Move the mouse pointer to the desired date in the calendar, then click on it. The date will automatically be entered into the From or To field.

Figure 11:
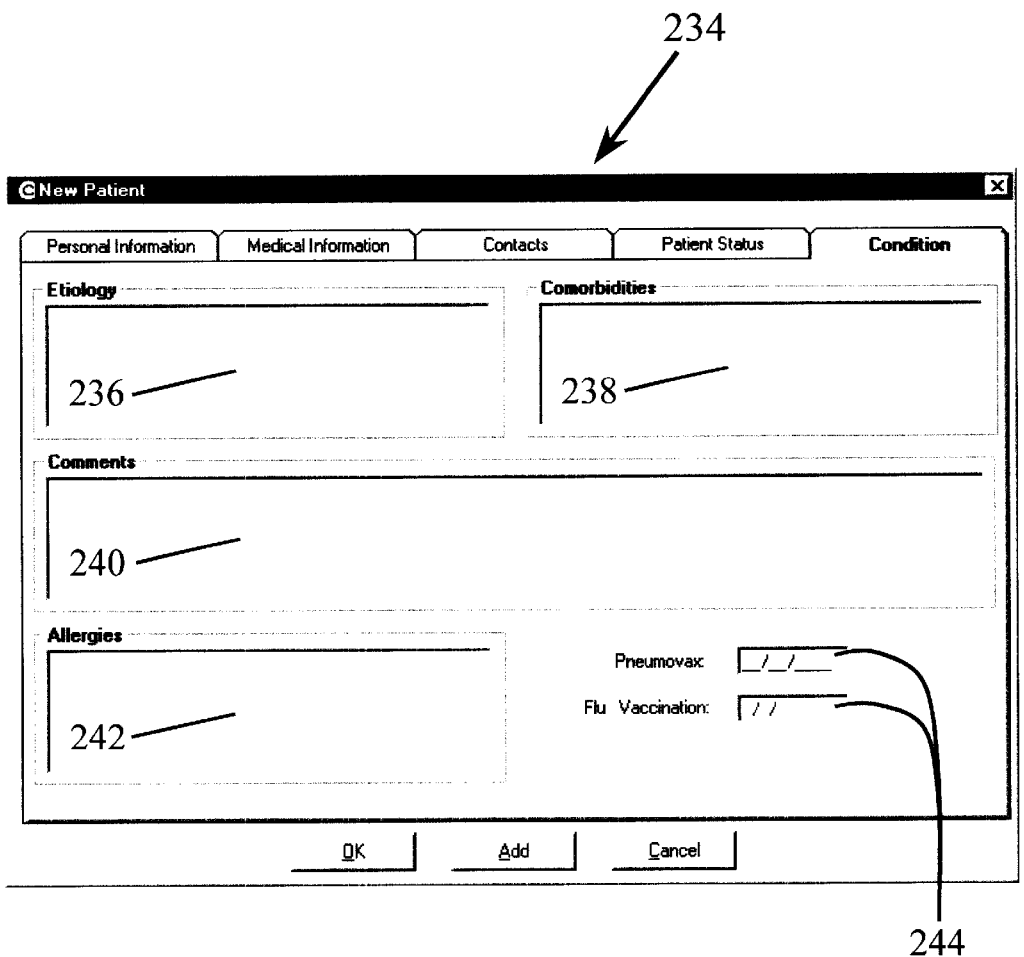
FIG. 11 is one example of a patient record computer user interface screen in accordance with the invention.

FIG. 11 illustrates an example of a Patient Condition screen 234 as it relates to permanent notes that should be stored in the patient's record. Permanent fields include: Etiology 236, Comorbidities 238, Comments 240, allergies 242, and the dates 244 of the patient's most recent vaccinations. This information is also entered in the appropriate fields.

When finished entering the patient information, the user may either return to the main menu or enter another patient record. Pressing OK enters the patient record into the system database and program execution returns to the main menu. Pressing Add allows the user to enter the patient record into the database 108 and continue entering additional patient records. Pressing Cancel allows the user return to the main menu. accordingly, no information will be entered.

Figure 12:
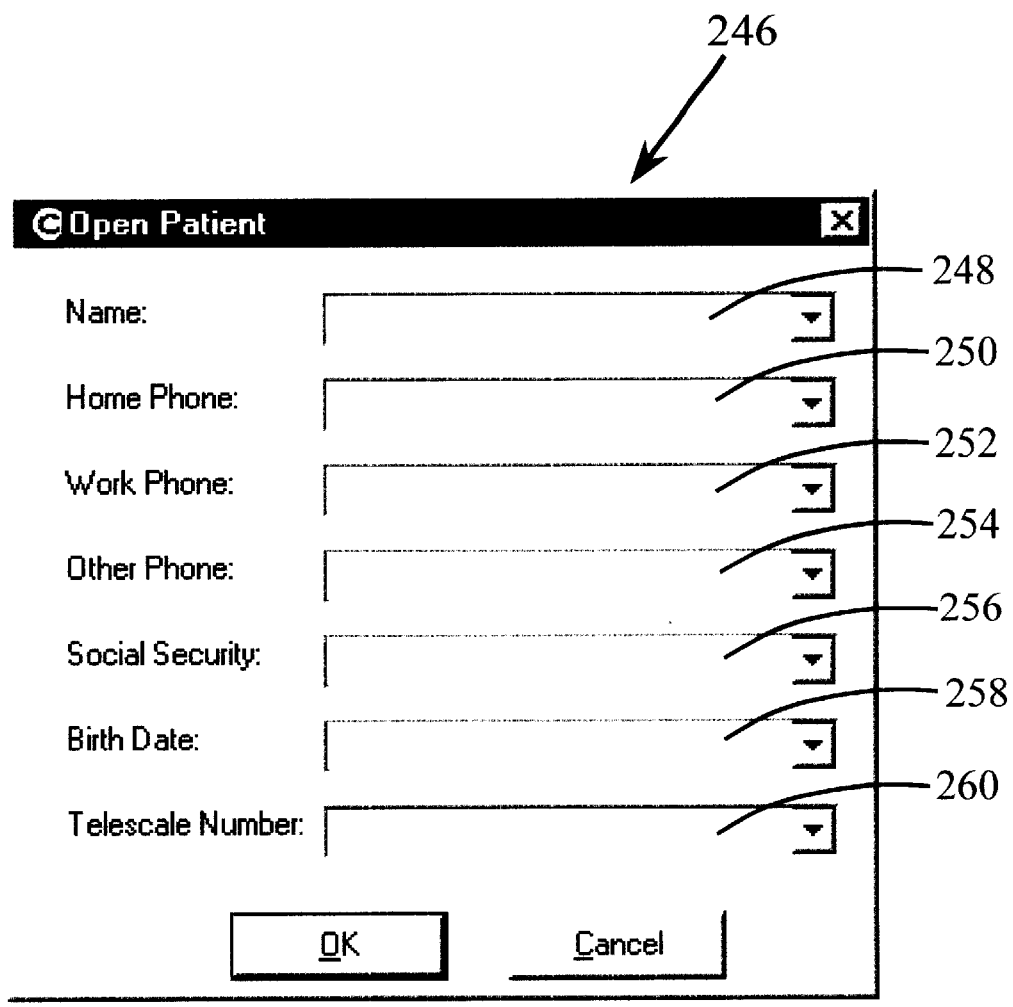
FIG. 12 is one example of a patient record computer user interface screen in accordance with the invention.

FIG. 12 illustrates one example of a patient record edit screen 246 in case there may be a need to update or change the information in a patient record the user may edit the database 108. To edit a Patient record the user may select File, Open, Patient on the menu bar or may click on the appropriate icon. To locate the desired record, the user may begin typing in a field unique to the patient or use the pull-down menus. Searchable fields include:

1) Name (Last, First) 248;

2) Home Phone 250;

3) Work Phone 252;

4) Other Phone 254;

5) Social Security Number 256;

6) Birth Date 258; and

7) TELESCALE™ Number 260 (Serial Number).

Once the desired record is located, the user may press OK. The Edit Patient screen 246 will then be displayed and the user may make the necessary changes in the patient record. Pressing OK saves the changes to the patient record. Otherwise, pressing Cancel returns the user to the main menu and no information will be changed.

Figure 13:
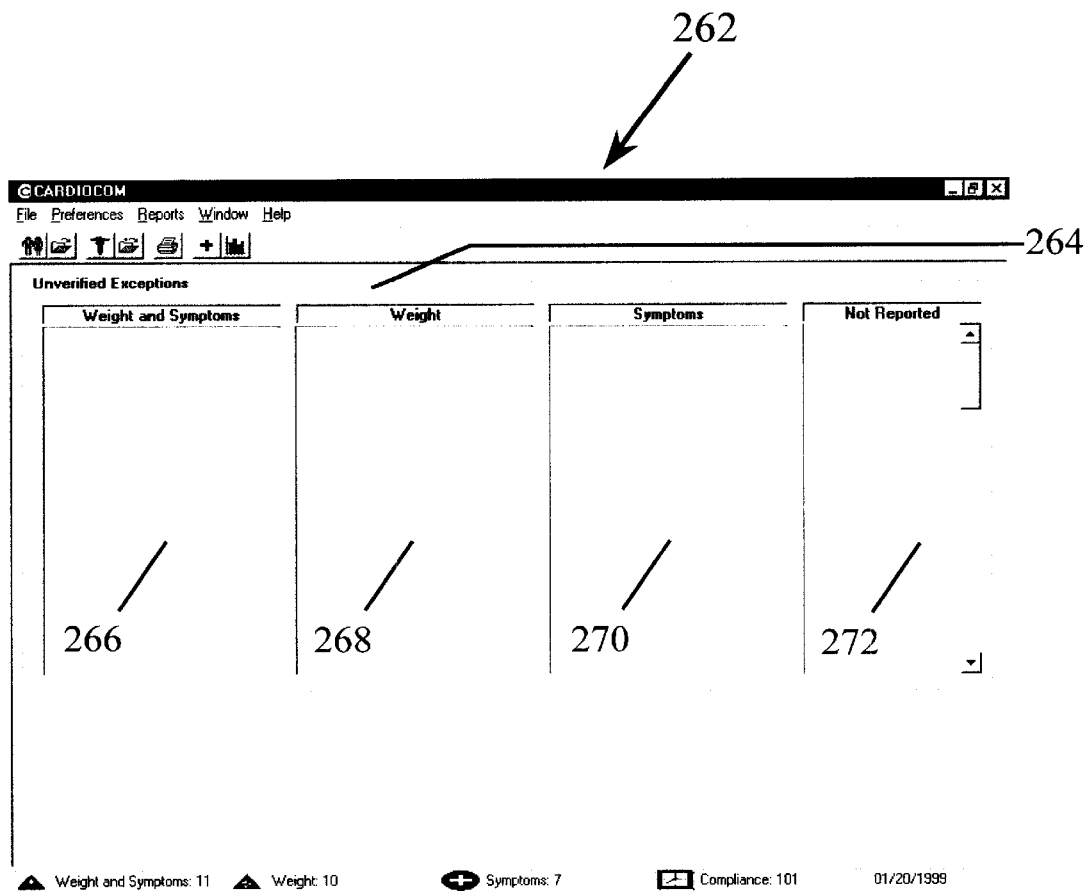
FIG. 13 is one example of a patient record computer user interface screen in accordance with the invention.

FIG. 13 illustrates one example of a monitoring screen 262 that allows easy viewing of patients which are categorized based on reported symptoms (the total score of reported symptoms). The user may simply double click on the patient's name and will be taken to the patient's unverified exception record. Monitoring patients includes viewing unverified exception fields 264 and resolving exceptions. For example, to resolve exceptions, the "Weight and Symptom" exceptions 266 are verified and "Not Reported" exceptions 272 are verified.

In one embodiment of the invention, patients requiring attention will appear in the Unverified Exceptions screen 264. These patients have been identified and categorized by:

1) Weight and Symptoms 266: patient is above their Maximum Allowed Weight+Trigger Weight Change AND has reported symptoms of CHF;

2) Weight 268: patient is above their Maximum Allowed Weight+Trigger Weight Change;

3) Symptoms 270: patient has reported symptoms of CHF; and

4) Not Reported 272: patient has not reported their daily Health Check.

The Unverified Exceptions screen 262 is the System's main menu and is always displayed. To go to Unverified Exceptions from another screen, the user may select Window, Unverified Exceptions or just click on it in the background. Patients who need to be contacted are listed in one of the following four columns:

1) Weight and Symptoms 266;
2) Weight 268;
3) Symptoms 270; and
4) Not Reported 272.

Once the System has issued an Exception, in order to resolve the Exception, the medical professional caregiver will need to contact the patient, verify the problem, and notify the physician or health professional as necessary. At the beginning of each day, all patients who have not reported their Health Check will appear in the Not Reported column.

In one embodiment of the invention, to verify a weight and/or symptom exception the user may click on the patient's name in the Unverified Exceptions screen. This will take the user directly to the Exception Verification screen.

Figure 14:
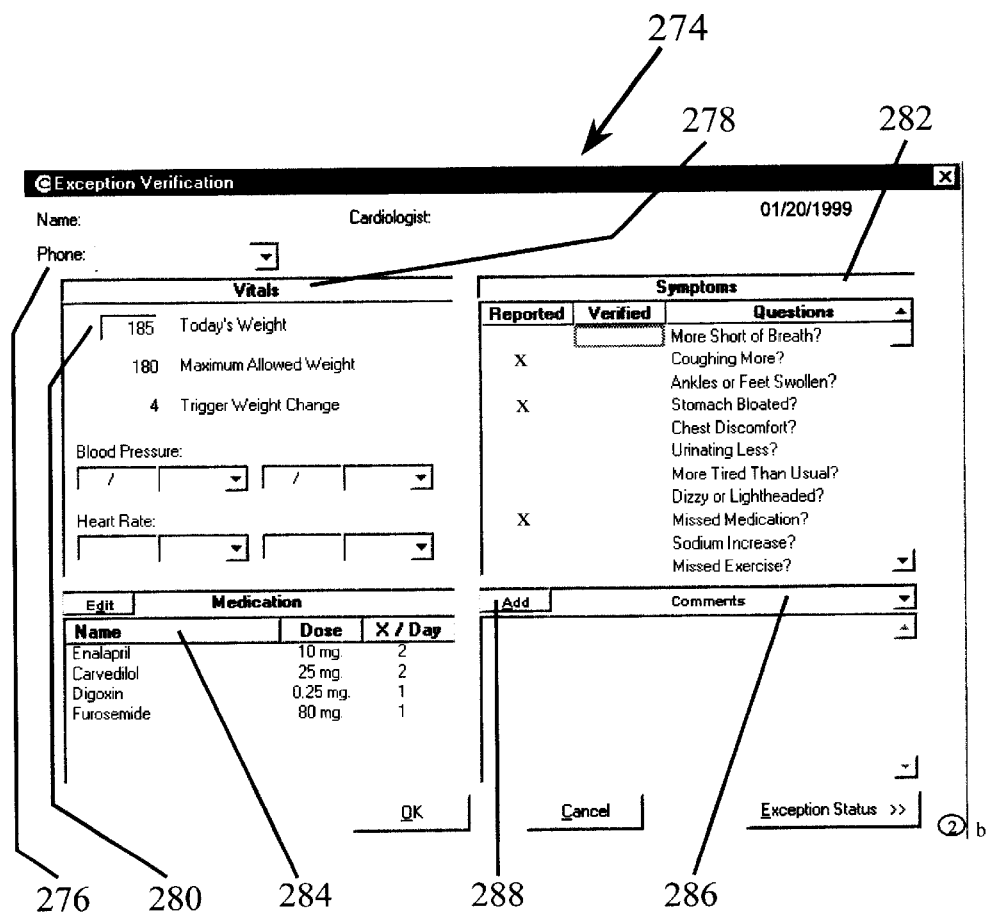
FIG. 14 is one example of an exception verification computer user interface screen in accordance with the invention.

FIG. 14 illustrates one embodiment of an Exception Verification Screen 274. Once at the Exception Verification screen 274, the user may verify and record the patient's weight, symptoms, and medications.

Subsequently, the user will contact the patient by telephone. The patient's telephone number 276 is listed in the top left-hand corner under the patient's name. Once the patient has been contacted, the user then goes to the Vitals and Symptoms section 278 and may verify the information reported in from the patient home monitoring apparatus. The caregiver may verify this data during the review process with the patient.

During the process, the user then goes to the Symptoms section 282. If the patient has reported a specific symptom, the Reported field adjacent to that question will display an "X" and the question will be highlighted in bold. The user will confirm all of the patient's Health Check answers.

The user then goes to the Medication section 284. The Medication section 284 asks the patient if he/she has been taking the medications in the doses and frequencies listed. If the patient has not been taking their medications as specified, the user will state the discrepancy in the Comments section 286. If the physician has revised the medication regimen, the user will make the appropriate changes by selecting Edit Medications.

The user then goes to the Comments section 286. The user has the option of adding multiple types of comments for the patient. These comments include: Impression, Nurse Assessment, Plan and Comments. The user may add to the patient's information by clicking the mouse on the Add button 288. The comment entry window will then appear. The user may then proceed to enter notes in the Nurse Assessment, Comments and Plan boxes. Pressing OK will date stamp and store the notes in the exception report in the database 108.

The user may view the Comments, Impression, Nurse Assessment or Plan information that was just entered. The user may also view the previous comments by type. The Exception Report is a document that alerts the physician when the patient's reported symptoms and/or weight is outside predetermined limits; or when the patient does not report their daily Health Check. Now the Exception Report is ready to be printed. The Exception Report is stored in the database 108.

Figure 15:
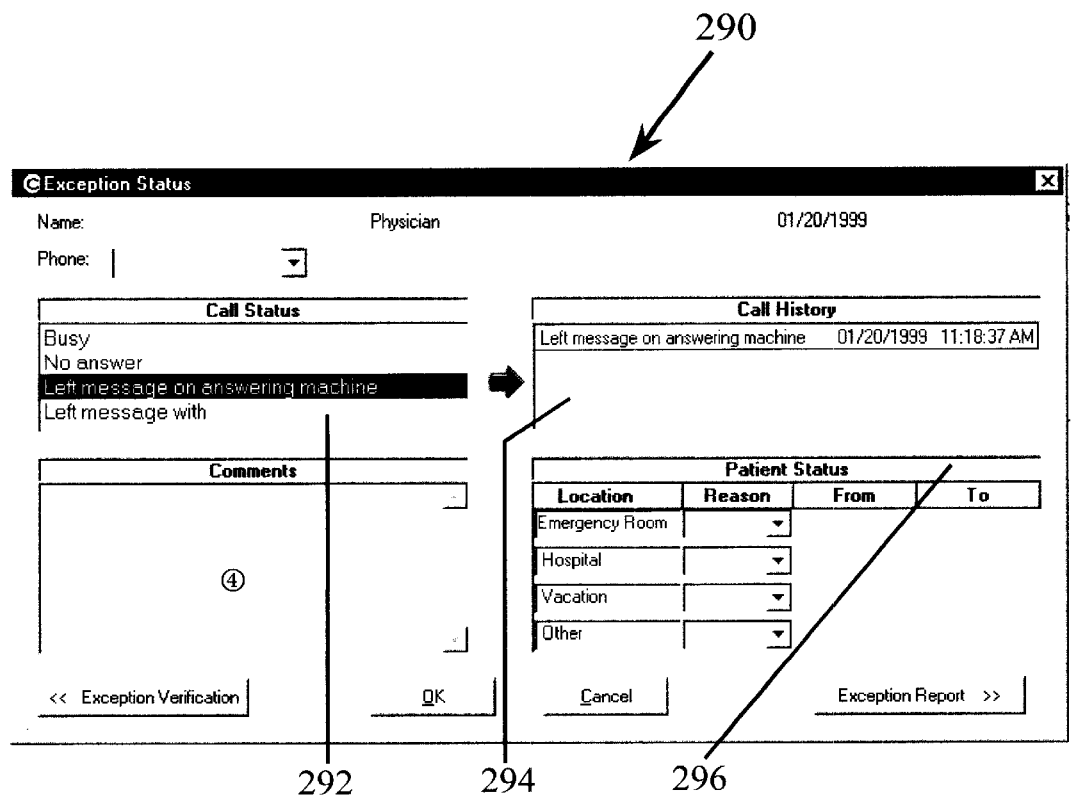
FIG. 15 is one example of an exception status computer user interface screen in accordance with the invention.

FIG. 15 illustrates one embodiment of an Exception Status Screen 290. To verify a Not Reported Exception the user should click on the patient's name in the Unverified Exceptions screen 262. This will take the user directly to the Exception Status screen 290. The Exception Status screen 290 is used to record the user's attempts to contact the patient and the patient's current status. The user must then call the patient at the patient's telephone number listed in the top left-hand corner. If the user is unable to speak with the patient, the user records the reason along with the date and time. In one embodiment of the invention, a double click on one of the following actions in the Call Status section 292: Busy; No Answer; Left message on answering machine; or Left message with (name of person) will record the information along with date and time in the Call History box 294.

If the user is able to speak with the patient, the user will ask them why they have not used the patient monitoring apparatus 102. Accordingly, the user will record the reason in the Comments box. Then, the user should ask the patient to complete the Health Check using the patient monitoring apparatus 102. Otherwise, the user may verify the patient's weight and symptoms during this phone call by pressing the Exception Verification button on the bottom left side of the screen. Pressing OK, returns the program to the Unverified Exceptions screen 262. The patient's name will remain in the Not Reported column 272 in the Unverified Exceptions screen 262 until the user is able to obtain the patient's Health Check information. An Exception Report will not be issued.

If there is a change in the patient's status, the user can record this information in the Patient Status section 296 by choosing one of the following locations: ER (Emergency Room); Hospital; Vacation; or Other. The user should then enter the Reason the patient is unable to use the System by double-clicking on the Reason field and selecting one of the three choices: CHF, Cardiac or Other. The date is then entered in the From box. If no date is entered, the System will automatically enter the current date. The date the patient will be returning is then entered in the To box (If you do not enter a date, the System will enter the same date that is in the From box.).

In one embodiment of the invention, an Exception Report may be a document that alerts the physician or healthcare professional to significant changes that have occurred in a patient's weight and wellness after the reported information has been verified by the user. It is also used to identify patients who have not reported their Health Check. Exception Reports can be viewed on the screen and printed for physician review.

To View Exception Reports the user may go to Reports, Exception on the menu bar or may click on the appropriate icon. Using the scroll down menu bar, the user then selects the last name of the patient whose Exception Report the user wishes to view. Pressing View displays the Exception Report for that patient. Otherwise, pressing Cancel returns the user to the main menu.

Figure 16:
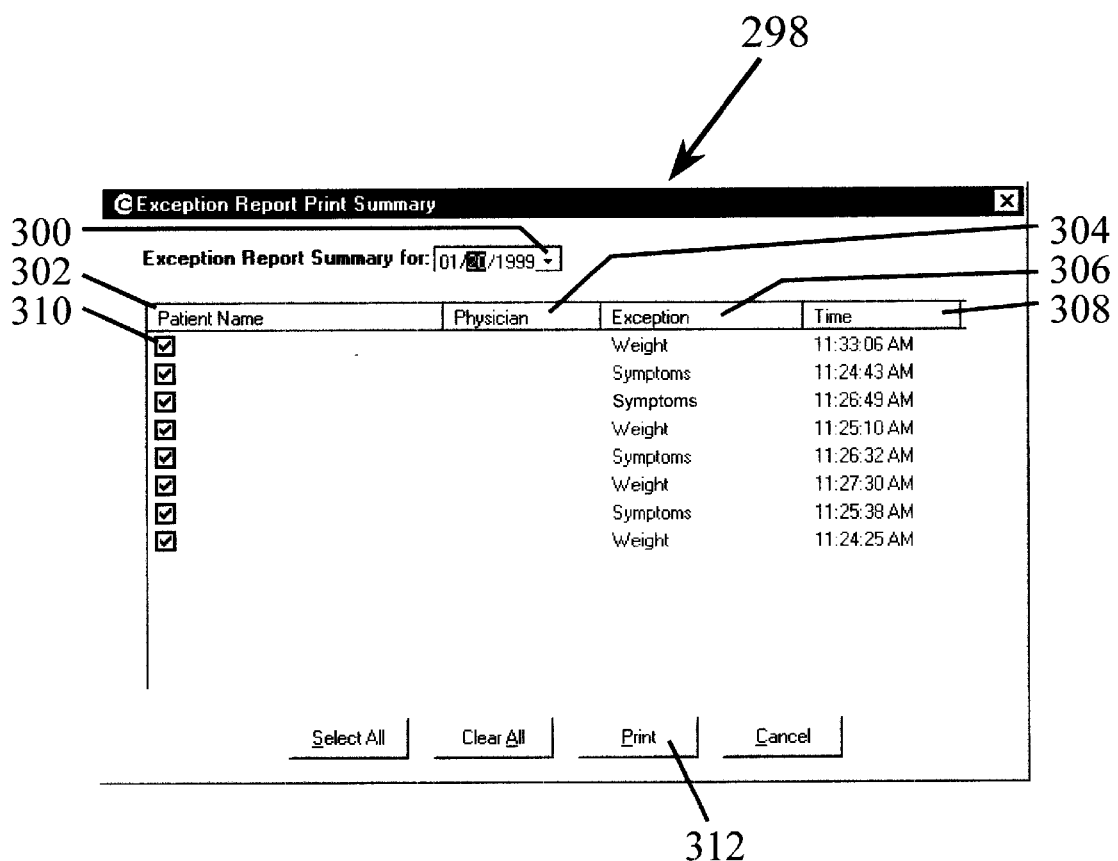
FIG. 16 is one example of an exception report print summary computer screen in accordance with the invention.

To print Exception Reports the user goes to File, Print, Exceptions on the menu bar. Accordingly, the Exception Report Print Summary screen 298, as illustrated in FIG. 16, will be displayed. In the Exception Report Print Summary is a list of all Exception Reports issued for a specific date. The current date will be displayed in the date field 300. If a different date is desired, the user selects the pull-down calendar or type in a new date.

The Exception Report Print Summary may be sorted. To do so, the user clicks on any part of the column header and the information will be sorted by: Patient's Last Name 302, Physician's Last Name 304, Exception Type 306, and Time Exception Issued 308. To sort in reverse order, the user may click on the column header again.

Exception Reports that have not been printed will appear with a checkmark 310 next to the patient's name. The user may choose to print the Exception Reports that have not been printed, any individual Exception Report, or all of the Exception Reports. To Print an Exception Report the user needs to identify the patient(s) and click on the box next to the patient(s) name. A check mark (☑ 310) will appear in the box(es) next to the name(s) selected. Pressing Print 312 will cause the selected Exception Report(s) to print. The user may print Exception Reports for all patients displayed by pressing the Select All button.

Figure 17:
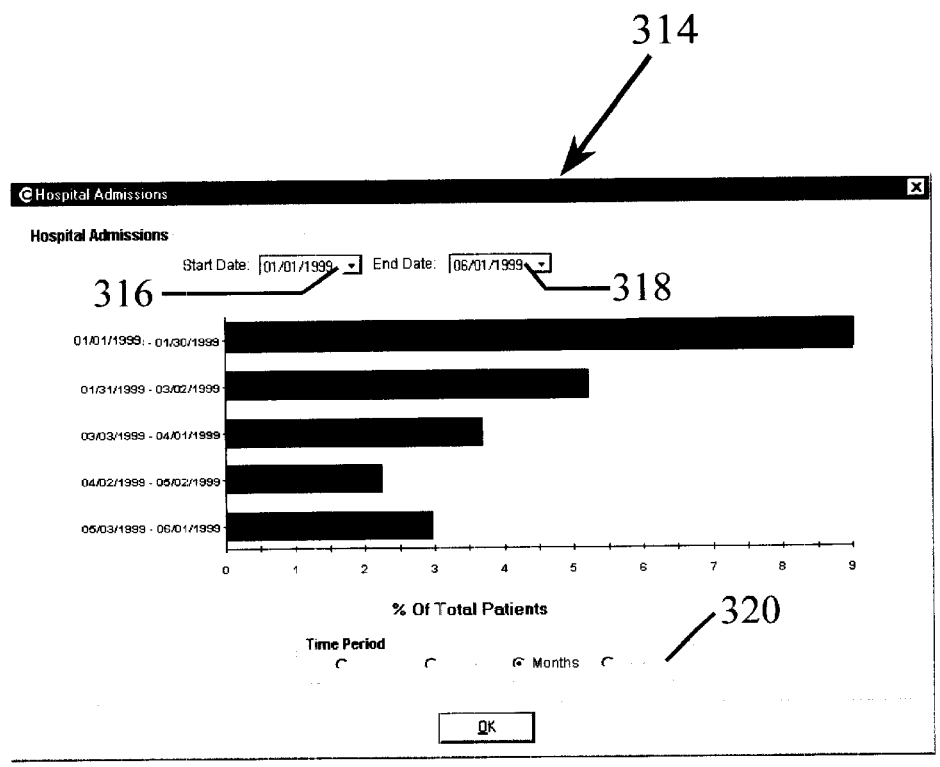
FIG. 17 is one example of trend report computer screen in accordance with the invention.

FIG. 17 illustrates one embodiment of a screen 314 of Trend Reports that may be generated for: hospital admissions; emergency room admissions; reported symptoms; patient summary; and hospital admissions. The Hospital Admissions Trend Report provides the user with a snapshot of the percent of total patients stored in the database 108 that are admitted to the hospital. This trend can be viewed on a daily, weekly, monthly, or annual basis for any specified time period. The percent of total measurement is not affected by changes in the actual number of patients under management. This feature can help measure the effectiveness of your CHF management program.

The user then selects the desired time period by specifying the Start Date and End Date. A calendar will appear by clicking on the pull down menu in the Start Date 316 or End Date 318 fields. By moving the mouse pointer to the desired date in the calendar, and clicking on it, the date will automatically be entered into the selected date field. The resolution of the data may be selected by using the buttons 320 on the bottom of the graph. Depending on the space available and number of date entries, the data can be viewed in Days, Weeks, Months, or Years. The user may print the Trend Report by selecting File, Print, Window or clicking on the appropriate icon. To view the Reason the user may single click-on any trend bar. The % of Total Patients by reason (CHF, Cardiac or Other) for the Hospital Admission will appear.

The user may also view the Emergency Room Trend Report which provides the user with a snapshot of the percent of total patients using the System in accordance with the present invention that are admitted to the emergency room. This trend may be viewed on a daily, weekly, monthly, or annual basis for any specified time period. The percent of total measurement is not affected by changes in the actual number of patients under management. This feature can help measure the effectiveness of your CHF management program.

To view the Emergency Room Admissions Trend Report, the user may select Reports, Trend, Emergency Admissions on the menu bar or click on the appropriate icon. The user the may select the desired time period to view by specifying the Start Date and End Date. A calendar will appear by clicking on the pull down menu in the Start Date or End Date fields. By moving the mouse pointer to the desired date in the calendar and clicking on it, the date will automatically be entered into the selected date field. The resolution of the data may be selected by using the buttons on the bottom of the graph. Depending on the space available and number of date entries, the data can be viewed in Days, Weeks, Months, or Years. To print the Trend Report the user selects File, Print, Window or may click on the appropriate icon. To View the Reason the user may single click-on any trend bar. The % of Total Patients by reason (CHF, Cardiac or Other) for the Emergency Room Admission will appear.

The Reported Symptoms Trend Report provides the user with a snapshot of the percent of total reported symptoms by individual symptom. This trend can be viewed for "all patients" or "only patients who required an Exception Report." This trend can be viewed on a daily, weekly, monthly, or annual basis for any specified time period. The percent of total measurement is not affected by changes in the actual number of patients under management.

To View the Reported Symptoms Trend Report, the user selects Reports, Trend, Reported Symptoms on the menu bar or may click on the appropriate icon. The user then chooses the patient group to view by selecting either: All Patients, or Exception Patients Only. Then, the user may select the desired time period to view by specifying the Start Date and End Date. A calendar will appear by clicking on the pull down menu in the Start Date and End Date fields. By moving the mouse pointer to be desired date in the calendar and clicking on it, the date will automatically be entered into the selected date field. To print the Trend Report the user selects File, Print, Window or may click on the appropriate icon.

Figure 18:
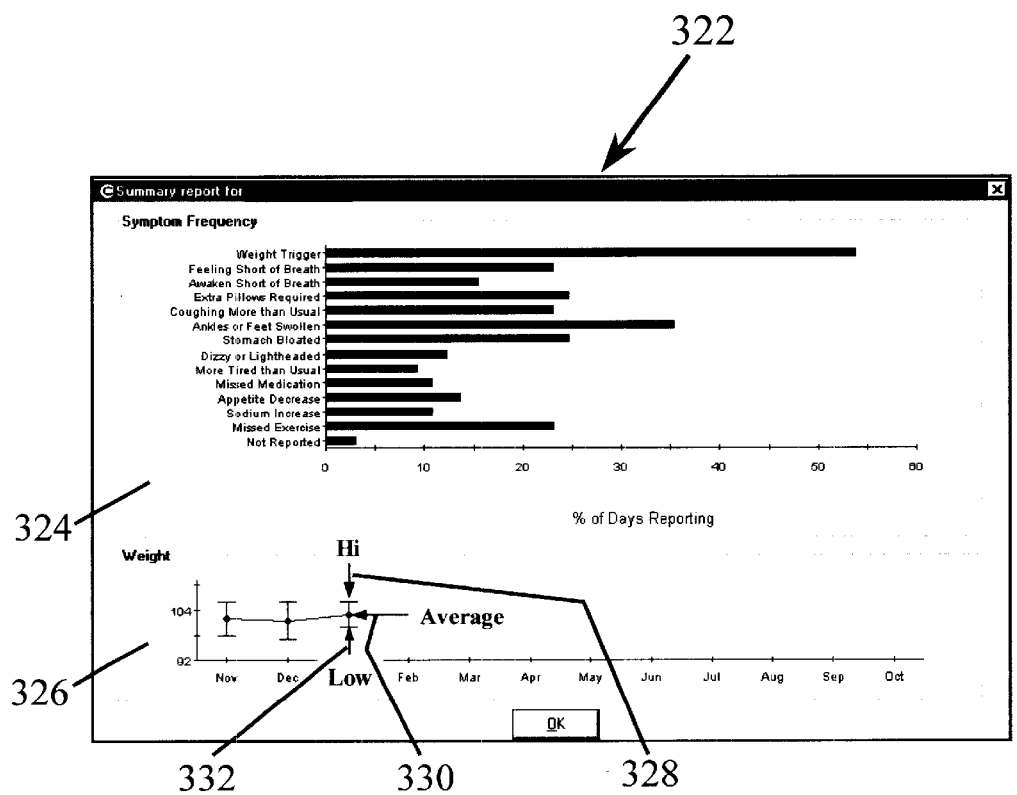
FIG. 18 is one example of a patient summary trend report screen in accordance with the invention.

FIG. 18 illustrates one embodiment of a Patient Summary Trend Report 322 which provides the user with a snapshot of an individual patient's symptoms 324 and weight measurements 326. This report plots individual symptoms 324 reported as a percent of total days the patient has been monitored by the system 100. The percent of total measurement is not affected by the actual number of days the patient has been under management. This trend report also plots the High 328, Average 330 and Low 332 monthly weight. To View the Patient Summary Trend Report the user selects Reports, Trend, Patient Summary on the menu bar or may click on the appropriate icon. The top part of the Patient Summary provides symptom frequency. The bottom part provides the High, Average and Low monthly weight measurement. To print the Trend Report the user selects File, Print, Window or may click on the appropriate icon.

FIG. 19 illustrates one embodiment of a Health Check Score 334 which is a numeric value that characterizes a patient's wellness. It is based on the patient's weight measurement and answers to the symptom questions 336. Each Health Check questions 336 has been assigned a relative value 338 from 1–10 based on symptom 340 severity. More severe symptoms 340 are assigned a higher relative value 338. The patient's weight measurement is compared to the Maximum Allowed Weight plus the Trigger Weight Change. If the patient's weight is greater than or equal to the Maximum Allowed Weight plus the Trigger Weight Change, then a value of 10 is assigned. If the total Health Check Score is greater than or equal to ten (10), an exception is issued. if the total health check score is less than ten (10), an exception is not issued.

Although a specific embodiment of the central computer software has been described, those skilled in the art will appreciate that other embodiments may be substituted in place thereof without departing from the scope and spirit of the present invention.

Process Description

FIG. 20 illustrates one embodiment of a process 342 that begins each day with the patient using the patient home monitoring apparatus 102 to complete the Health Check. The Health Check is a series of wellness questions and a weight measurement. This weight and wellness information is automatically transmitted from the patient home monitoring apparatus 102 to the central computer system 104. If significant symptoms and/or excessive changes in weight are reported, then an Exception Report is sent to the patient's physician. The physician or health professional resolves the problem directly with the patient.

The system in accordance with the present invention, follows a systematic decision making process to identify symptomatic patients. In one embodiment, a patient uses the patient monitoring apparatus 102 and patient completes the Health Check Box 344. The Health Check information is automatically transmitted by telephone from the patient monitoring apparatus 102 to the system 104. The answer to each Health Check question and the variance from the weight specified by the physician is assigned a score on the system 104. According to the patient's individual scores are totaled box 346. The process branches out based in the following decision. If the patient's total Health Check score is greater than or equal to ten (10), an Exception is issued. An Exception notifies the user that the patient requires attention due to a symptom and/or weight issue. An Exception will be also be issued if the patient does not report their daily Health Check.

If an Exception is issued, the user calls the patient to verify the Health Check information box 348. The Exception Report is sent to the physician or health professional box 350. As described above, an Exception Report is a document that alerts the physician when the patient reports significant symptoms and/or weight changes; or when the patient does not report their daily Health Check. Accordingly, the medical professional caregiver (e.g., physician or health professional) resolves the Exemption Report issue with the patient box 352.

Otherwise, if the patient's Health Check score is less than ten (10), the System will not issue an Exception since the patient's weight and symptoms are within an acceptable range. Accordingly, no Exception is issued and no action is required box 354.

Figure 21:
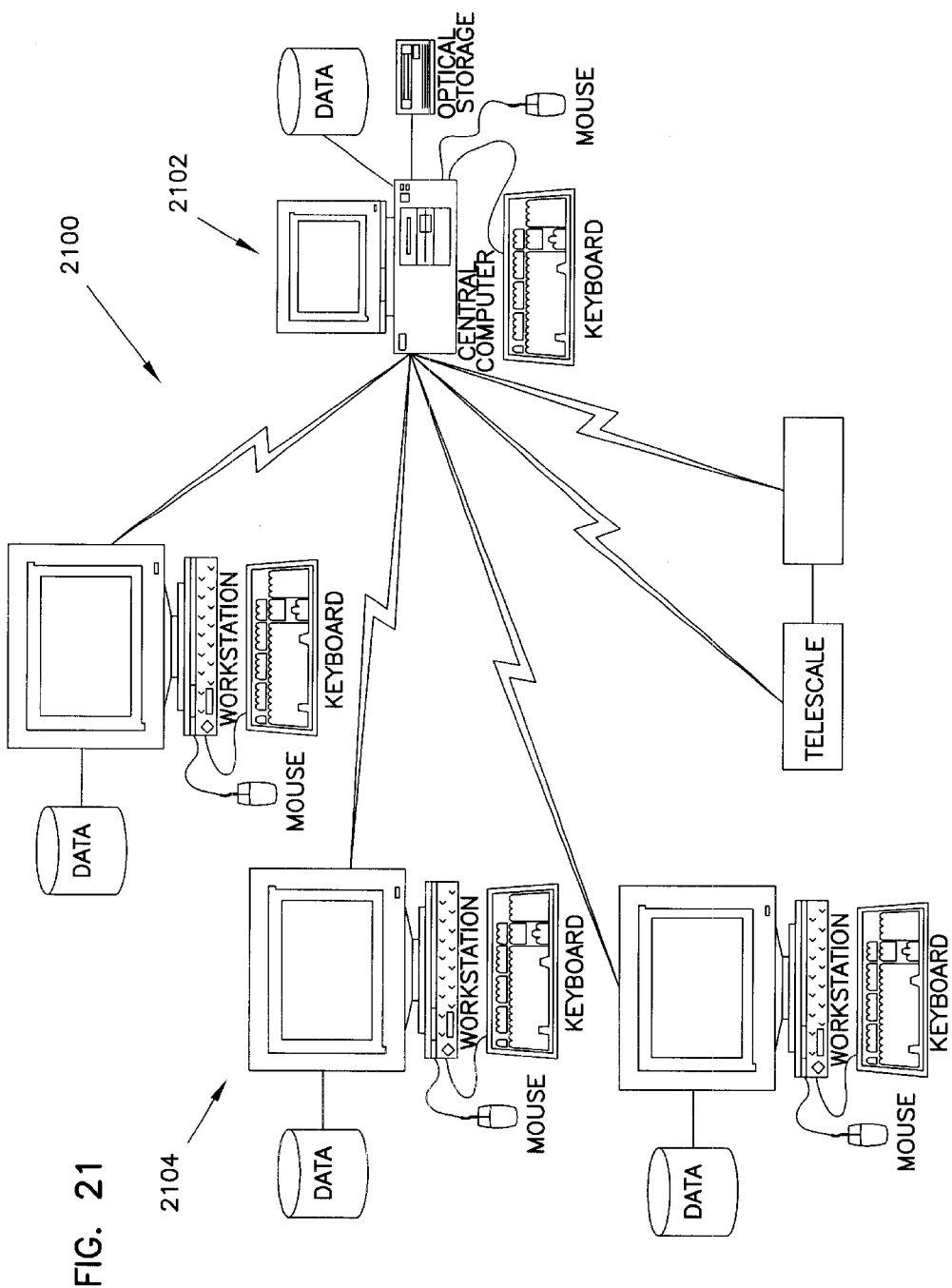
FIG. 21 is one example of a diagram of a hardware environment in accordance with the invention.

FIG. 21 is a diagram of a hardware environment used to implement one embodiment of the invention within a network architecture and, more particularly, illustrates a typical distributed computer system 2100 using a wide area network to connect the central computer system 2102 with the remote workstations computers 2104 (or terminals). Generally, a combination of resources may include central computers that are personal computers, workstations minicomputer or mainframe and a remote computer that is a personal computer, workstation, minicomputer or mainframe. These systems may be coupled to one another by various networks, including LANs, WANs, SNA networks and others. It will be appreciated that these networks include wireless and as well as wired networks.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

The claimed invention is:

1. A medical system for monitoring and managing one or more ambulatory patients on a computer and allowing a caregiver to review the ambulatory patients' wellness parameters to provide treatment in accordance with the wellness parameters, comprising:

a patient monitoring apparatus having a first communication device associated therewith for monitoring a patient's wellness parameters;

a central computer located remote from the monitoring apparatus and in communication therewith, the central computer having a second communication device associated therewith for communicating wellness parameters and treatment data over a communications link established between the central computer and the monitoring apparatus, the central computer being operated for querying the patient via the patient monitoring apparatus, receiving and processing measured wellness parameters from the monitoring apparatus and calculating a score according to the wellness parameters;

a main database coupled to the central computer having patient medical records stored therein; and one or more computer workstations located remote from the central computer and in communication therewith, the one or more computers having a third communication device associated therewith for communicating physical examination data between the central computer and the one or moire workstations over a communication link established therebetween;

wherein, the score calculated by the central computer according to the wellness parameters is compared with a predetermined value, and based on the results of the comparison the central computer issuing an exception report and communicating the exception report to the one or more workstations located remote therefrom, whereby a caregiver located at the remote workstation site is notified of the exception report; and wherein the central computer initiates and provides a notification or absence, during a pre-designated interval of time, of communication of the patient's wellness parameters.

2. The system according to claim 1, wherein the patient monitoring apparatus is configured and arranged to monitor the patient's weight.

3. The system according to claim 1, wherein the one or more workstations are located at any one of one or more health clinics, hospitals, emergency rooms and HMOs.

4. The system according to claim 1, further comprising:

a remote dial-in workstation located remote from the central computer and in communication therewith, the remote dial-in workstation having a fourth communication device associated therewith for communicating with the central computer and accessing the database.

5. The system according to claim 1, further comprising:

a second database located remote from the main database and having patient medical records stored therein, the second database being accessible by the central computer via a communication link established therebetween.

6. The system according to claim 5, wherein the second database includes the patient's hospital information data stored therein.

7. The system according to claim 1, wherein a telephone number is automatically downloaded into the home monitoring apparatus from a remote location.

8. A method for monitoring and managing one or more ambulatory patients on a computer and allowing a caregiver to review the ambulatory patients' wellness parameters to provide treatment in accordance with the wellness parameters, the method comprising;

receiving a patient's wellness parameters at a central computer from a patient monitoring apparatus located remote therefrom;

creating a patient medical record in a database coupled to the central computer and storing the patient's wellness parameters received from the monitoring apparatus into the database;

monitoring the patient's status;

calculating a score with the central computer based on the patient's wellness parameters;

comparing the score with a predetermined value;

based on the results of the comparison, issuing an exception report and communicating the report to one or more workstations located remote from the central computer, whereby a caregiver is notified of the exception report; and intiating a notification of absence, during a pre-designated interval of time, of communication of the patient's wellness parameters.

9. The method according to claim 8, wherein the patient monitoring apparatus is configured and arranged to monitor the patient's weight.

10. The method according to claim 8, wherein the one or more workstations are located at any one of one or more health clinics, hospitals, emergency rooms and HMOs.

11. The method according to claim 8, further comprising:

accessing a second database located remote from the main database and having patient medical records stored therein, the second database being accessible by the central computer via a communication link established therebetween.

12. The method according to claim 11, wherein the second database includes the patient's hospital information data stored therein.

13. The method according to claim 8, wherein upon being provided with an exception report, the caregiver:

contacting the patient;

verifying the condition that triggered the exception report; and making the appropriate adjustments to the patient's medication and/or fluid intake.

14. The method according to claim 13, further comprising notifying a physician of the patient's symptoms.

15. The method according to claim 8, wherein a telephone number is automatically downloaded into the home monitoring apparatus from a remote location.

16. An apparatus for monitoring and managing one or more ambulatory patients on a computer and allowing a caregiver to review the ambulatory patients' wellness parameters to provide treatment in accordance with the wellness parameters, the apparatus comprising:

a central computer located remote from a patient monitoring apparatus and in communication therewith, the central computer having a communication device associated therewith for communicating wellness parameters and treatment data over a communications link established between the central computer and the monitoring apparatus, the central computer being operated to query the patient via the patient monitoring apparatus, receiving and processing measured wellness parameters from the monitoring apparatus and calculating a score according to the wellness parameters received by the computer system, the computer system having one or more storage devices coupled thereto; and one or more computer programs, performed by the central computer for receiving a patient's wellness parameters at a central computer from a patient monitoring apparatus located remote therefrom, creating a patient medical record in a database coupled to the central computer and storing the patient's wellness parameters received from the monitoring apparatus into the database, monitoring the patient's status, calculating the score with the central computer based on the patient's wellness parameters, comparing the score with a predetermined value and based on the results of the comparison, issuing an exception report and communicating the exception report to one or more workstations located remote from the central computer, whereby a caregiver is notified of the exception report.

17. The apparatus according to claim 16, wherein the patient monitoring apparatus is configured and arranged to monitor the patient's weight.

18. The apparatus according to claim 16, wherein the one or more workstations are located at any one of one or more health clinics, hospitals, emergency rooms and HMOs.

19. The apparatus according to claim 16, further comprising:

accessing a second database located remote from the main database and having patient medical records stored therein, the second database being accessible by the central computer via a communication link established therebetween.

20. The apparatus according to claim 19, wherein the second database includes the patient's hospital information data stored therein.

21. The apparatus according to claim 16, wherein a telephone number is automatically downloaded into the home monitoring apparatus from a remote location.

22. An article of manufacture comprising a computer program carrier readable by a computer system having one or more processors and embodying one or more instructions executable by the computer system to perform a method for monitoring and managing one or more ambulatory patients on a computer and allowing a caregiver to review the ambulatory patients' wellness parameters and provide treatment in accordance with the wellness parameters, the method comprising:

receiving a patient's wellness parameters at a central computer from a patient monitoring apparatus located remote therefrom;

creating a patient medical record in a database coupled to the central computer and storing the patient's wellness parameters received from the monitoring apparatus into the database;

monitoring the patient's status;

calculating a score with the central computer based on the patient's wellness parameters;

comparing the score with a predetermined value;

based on the results of the comparison, issuing an exception report and communicating the exception report to one or more workstations located remote from the central computer, whereby a caregiver is notified of the exception report; and initiating a notification of absence, during a pre-designated interval of time, of communication of the patient's wellness parameters.

23. The article of manufacturing according to claim 22, wherein the patient monitoring apparatus is configured and arranged to monitor the patient's weight.

24. The article of manufacture according to claim 22, wherein the one or more work stations are located at any one of one or more health clinics, hospitals, emergency rooms and HMOs.

25. The article of manufacture according to claim 22, further comprising:

accessing a second database located remote from the main database and having patient medical records stored therein, the second database being accessible by the central computer via a communication link established therebetween.

26. The article of manufacture according to claim 25, wherein the second database includes the patient's hospital information data stored therein.

* * * * *